United States Patent
Leadbetter et al.

(10) Patent No.: US 10,881,720 B2
(45) Date of Patent: Jan. 5, 2021

(54) NANOPARTICLES FOR IMMUNE STIMULATION

(71) Applicants: THE BOARD OF REGENTS OF THE UNIVERSITY OF TEXAS SYSTEM, Austin, TX (US); RENSSELAER POLYTECHNIC INSTITUTE, Troy, NY (US)

(72) Inventors: Elizabeth Leadbetter, Saranac Lake, NY (US); Eyal Amiel, Hinesburg, VT (US); Emilie Vomhof-Dekrey, Grand Forks, ND (US); Robert Lindhardt, Troy, NY (US); Amanda MacDonald, Cambridge, MA (US); Jianjun Maio, Woodbridge, NJ (US)

(73) Assignees: THE BOARD OF REGENTS OF THE UNIVERSITY OF TEXAS SYSTEM, Austin, TX (US); RENSSELAER POLYTECHNIC INSTITUTE, Troy, NY (US)

( * ) Notice: Subject to any disclaimer, the term of this patent is extended or adjusted under 35 U.S.C. 154(b) by 0 days.

(21) Appl. No.: 15/115,466

(22) PCT Filed: Jan. 29, 2015

(86) PCT No.: PCT/US2015/013441
§ 371 (c)(1),
(2) Date: Jul. 29, 2016

(87) PCT Pub. No.: WO2015/116775
PCT Pub. Date: Aug. 6, 2015

(65) Prior Publication Data
US 2017/0165345 A1 Jun. 15, 2017

Related U.S. Application Data

(60) Provisional application No. 61/933,361, filed on Jan. 30, 2014.

(51) Int. Cl.
*A61K 39/09* (2006.01)
*A61K 9/51* (2006.01)
*A61K 39/39* (2006.01)
*A61K 9/127* (2006.01)
*A61K 39/00* (2006.01)

(52) U.S. Cl.
CPC ............ *A61K 39/092* (2013.01); *A61K 9/127* (2013.01); *A61K 9/5153* (2013.01); *A61K 9/5192* (2013.01); *A61K 2039/55555* (2013.01); *A61K 2039/55572* (2013.01); *A61K 2039/575* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2010/0285135 A1* | 11/2010 | Wendorf | A61K 9/5153 424/489 |
| 2012/0021050 A1* | 1/2012 | Zhou | A61K 39/39 424/451 |
| 2012/0114677 A1 | 5/2012 | Zepp | |

OTHER PUBLICATIONS

Berti et al., ACS Chem Biol., 8, pp. 1653-1663. (Year: 2013).*
International Search Report issued in International Application No. PCT/US2015/013441 dated Jul. 13, 2015.
Written Opinion of the International Search Searching Authority issued in International Application No. PCT/US2015/013441.
Federica Sarti et al. "In vivo evidence of oral vaccination with PLGA nanoparticles containing the immunostimulant monophosphoryl lipid A" Biomaterials, vol. 32, No. 16, Feb. 9, 2011, pp. 4052-4057.
Hamdy, S. et al. "Co-delivery of cancer-associated antigen and Toll-like receptor 4 ligand in PLGA nanoparticles induces potent CD8<+> T cell mediated anti-tumor immunity" Vaccine, vol. 26, No. 39, Sep. 15, 2008, pp. 5046-5057.

* cited by examiner

*Primary Examiner* — Abigail Vanhorn
(74) *Attorney, Agent, or Firm* — Womble Bond Dickinson (US) LLP

(57) ABSTRACT

The invention relates, in part, to nanoparticles, methods for preparing nanoparticles and methods of administering nanoparticles for immune stimulation. An immune-stimulating nanoparticle of the invention may include, at least in part, a polymer substrate comprising a biodegradable polymer and may include at least one antigen and/or at least one adjuvant.

3 Claims, 6 Drawing Sheets

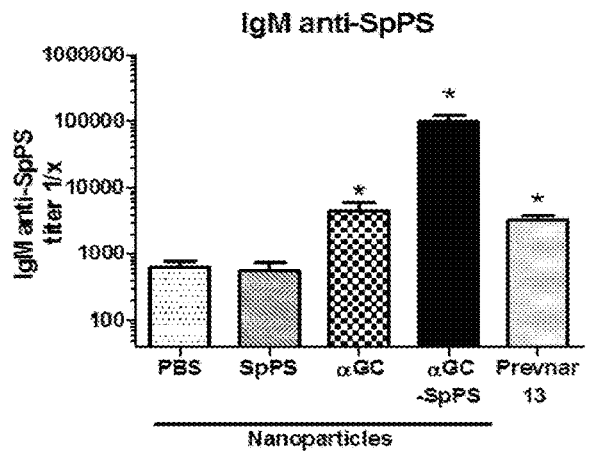
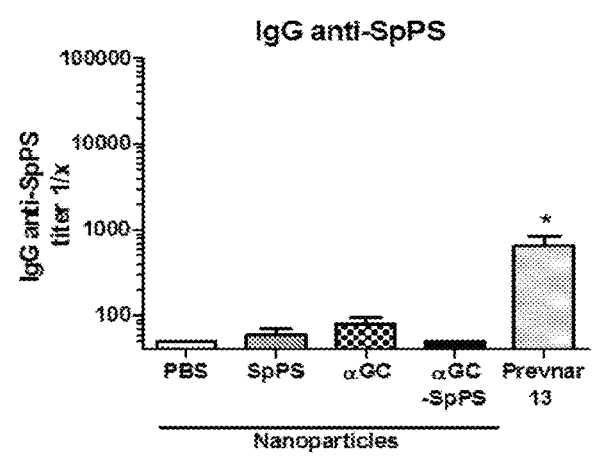
Fig. 4A
Fig. 4B
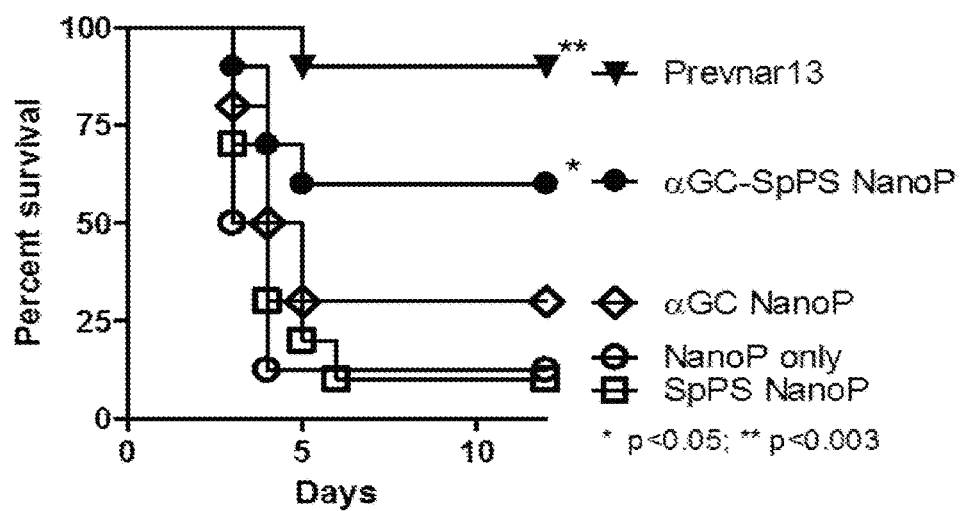
Fig. 4C

NANOPARTICLES FOR IMMUNE STIMULATION

CROSS-REFERENCE TO RELATED APPLICATIONS

This application is a National Stage Entry of International Application No. PCT/US2015/013441, filed on Jan. 29, 2015, and claims the benefit of and priority to U.S. 61/933,361, filed Jan. 30, 2014, which are hereby incorporated by reference into this application in their entirety.

GOVERNMENT INTEREST

This invention was made with government support under T32 AI049823-13 awarded by the National Institutes of Health. The Government has certain rights in the invention.

FIELD OF THE INVENTION

The invention relates, in part, to methods for preparing and administering nanoparticles for immune stimulation.

BACKGROUND

Currently available vaccines for *S. pneumoniae* contain protein-conjugated or unconjugated mixtures of polysaccharides from prevalent serotypes. Both Pneumovax (Merck & Co, Inc.) containing 23 serotypes of unconjugated polysaccharides and Prevnar13@ (Wyeth Pharmaceuticals/Pfizer, Inc.), containing 13 serotypes of polysaccharides conjugated to diptheria toxin proteins (CRM 197) and mixed with alum adjuvant, are efficacious but costly to produce, and leave the patient open to infection with increasingly prevalent non-vaccine serotypes. *S. pneumoniae* continues to be a significant cause of morbidity and health care costs in industrialized nations and the developing world due to lack of access to these expensive vaccines or infection with non-vaccine serotypes.

Various liposome and nanoparticle formulations have been attempted in efforts to prepare effective vaccines. The adjuvant αGalCer has been utilized in some formulations but such efforts have been complicated by studies showing that soluble αGalCer can induce anergy in iNKT cells in the mouse system [Fujii, S., et. al., 2002 *Nature immunology* 3:867-874; Matsuda, J. L., et. al., 2003 *Proceedings of the National Academy of Sciences of the United States of America* 100:8395-8400; Parekh, V. V., et. al., 2005, *The Journal of clinical investigation* 115:2572-2583; and Singh, N., et. al., 1999 *Journal of Immunology* 163:2373-2377] especially if presented by B cells in the absence of co-stimulatory molecules [Bezbradica, J. S., et. al., 2005 *Journal of immunology* 174:4696-4705; Schmieg, J., et. al., 2005 *Proceedings of the National Academy of Sciences of the United States of America* 102:1127-1132; and Toura, I., et. al., 1999 *Journal of immunology* 163:2387-2391]. Some prior formulations have utilized poly(lactic-co-glycolic) acid (PLGA) polymers and have also included surface modification by PEGylation [Danhier, F., et. al., 2010 *Journal of controlled release: official journal of the Controlled Release Society* 148:135-146] or chitosan coating [Tahara, K., et. al., 2009 *International Journal of Pharmaceutics* 382: 198-204].

Although some vaccine particles and liposomes have been developed that include "stealth" coatings to increase the time the particle or liposome remains in circulation or is retained in plasma or tissues after administration to a subject, this is not optimal for many vaccines. For example, prolonged retention in plasma or tissue of stealth particles or liposomes may lead to adverse conditions in a subject, such as, for example, hand/foot syndrome, or other rate-limiting toxicity. Another difficulty associated with previous vaccine particles and liposomes has been a rapid burst of drug release at the time of administration, which is common for nanoparticles with drugs or antigens loaded on their surface. These and other drawbacks limit the usefulness of some existing liposomes and particles.

SUMMARY OF THE INVENTION

The present invention, in part, relates to nanoparticles methods of making and administering nanoparticles, and their use in treating diseases and conditions.

According to one aspect of the invention, nanoparticles are provided that include a polymer substrate, wherein the polymer substrate includes a biodegradable polymer and at least one antigen and the nanoparticle also includes at least one adjuvant in the nanoparticle core. In some embodiments, at least a portion of the at least one antigen is positioned external to the outer surface of the nanoparticle. In certain embodiments, at least a portion of the at least one antigen in the polymer substrate is positioned internal to the outer surface of the nanoparticle. In some embodiments, the biodegradable polymer is poly(lactic-co-glycolic acid) (PLGA). In some embodiments, the nanoparticle has a diameter of less than 100 nm. In some embodiments, the nanoparticle has a diameter between 100 nm and 900 nm. In certain embodiments, the adjuvant is a natural or synthetic alphaGalactosylceramide compound or functional variant thereof. In some embodiments, the adjuvant is a CD1d-presented iNKT cell glycolipid agonist. In some embodiments, the adjuvant is a CD1d-independent iNKT cell agonist. In certain embodiments, the CD1d-independent iNKT cell agonist is a Toll-Like Receptor ligand, an imidazoquinolone compound, lipopeptide Pam3Cys-Ser-(Lys)4, cytosine-guanine dinucleotides (CpG) or a bacterial component (such as monophosphoryl lipid A, MPLA). In some embodiments, the Toll-Like Receptor is Toll-like Receptor 3, 4, 7, or 9. In some embodiments, the antigen is a microbial antigen, a cancer antigen, an autoimmune antigen, or an environmental antigen. In some embodiments, the microbial antigen is a bacterial antigen, a fungal antigen, a parasitic antigen, or a viral antigen. In certain embodiments, the bacterial antigen is an encapsulated bacteria antigen. In some embodiments, the antigen is a Streptococcal antigen, a *Candida* antigen, a *Cryptococcus* antigen, a *Brucella* antigen, a *Salmonella* antigen, a Staphylococcal antigen, a *Porphyromonas* antigen, a *Burkholderia* antigen, a *Bacillus* antigen, a Mycobacteria antigen, a *Shigella* antigen, a *Pseudomonas* antigen, a *Bordetella* antigen, a *Clostridium* antigen, a Norwalk virus antigen, a *Bacillus anthracis* antigen, a *Mycobacterium tuberculosis* antigen, a human immunodeficiency virus (HIV) antigen, a *Chlamydia* antigen, a human Papillomavirus antigen, an Influenza virus antigen, a Paramyxovirus antigen, a Herpes virus antigen, a Cytomegalovirus antigen, a Varicella-Zoster virus antigen, an Epstein-Barr virus antigen, a Hepatitis virus antigen, a *Plasmodium* antigen, a *Trichomonas* antigen, a sexually transmitted disease antigen, an aerosol-transmitted disease antigen, a viral encephalitis disease antigen, a protozoan disease antigen, a fungal disease antigen, a bacterial disease antigen, a tumor antigen, or a cancer antigen. In some embodiments, the encapsulated bacteria is *Haemophilus influenza* type B, *Streptococcus pneumoniae*, *Neisseria men-* ingitidis, Group B streptococcus (GBS), *Klebsiella pneumonia, Staphylococcus aureus, Pseudomonas aeruginosa, Burkholderia pseudomallei, Burkholderia mallei, Escherichia coli, Bacteroides fragilis,* or *Salmonella typhi.* In some embodiments, the nanoparticle also includes a B-cell population-targeting antigen. In certain embodiments, the B-cell population-targeting antigen includes a polysaccharide, a glycan, an oligonucleotide, a lipopeptide, a protein, a peptide, or a combination of two or more thereof. In some embodiments, the nanoparticle also includes a pathogen-derived polysaccharide antigen. In some embodiments, the polymer substrate includes at least 2, 3, 4, 5, 6, 7, 8, 9, 10, 25, 50, 60, 70, 80, 90, 100, 125, 150, 175, or 200 different antigens. In certain embodiments, wherein the nanoparticle core includes at least 2, 3, 4, 5, 6, 7, 8, 9, or 10 different adjuvants. In some embodiments, the nanoparticle is not a liposome, does not include a lipid bilayer, is not modified on the surface with polyethylene glycol (PEG), and is not associated with a lipid bilayer.

According to another aspect of the invention, methods of immune stimulation in a subject are provided. The methods include administering to a subject in need of immune stimulation a composition that includes any aforementioned embodiment of a nanoparticle of the invention, in a dose effective to stimulate in the subject an immune response specific to the nanoparticle's at least one antigen. The invention, in certain aspects also provides methods of treating a disease or condition in a subject, and the methods include administering to a subject in need of such treatment a composition including any embodiment of an aforementioned nanoparticle of the invention, in a dose effective to treat the disease or condition in the subject. In some embodiments, the dose is effective to prevent or treat a microbial disease or condition, cancer, or an autoimmune disease or condition in the subject. In some embodiments of the aforementioned aspects, the dose is between 1 femtogram and 5 milligram of adjuvant and between 1 femtogram and 5 milligram antigen. In some embodiments of the aforementioned aspects, the adjuvant is a glycolipid adjuvant and the antigen is a B cell antigen. In certain embodiments of the aforementioned aspects, the subject is a human. In some embodiments, the adjuvant is a glycolipid adjuvant. In certain embodiments of the aforementioned aspects, the polymer includes at least one bacterial polysaccharide. In some embodiments of the aforementioned aspects, the at least one antigen and the least one adjuvant function cooperatively to elicit the immune response. In some embodiments of the aforementioned aspects, the method also includes administering one or more additional nanoparticles of any of the aforementioned embodiments.

According to another aspect of the invention, pharmaceutical compositions are provided that include one or more of any of the aforementioned embodiments of a nanoparticle of the invention, and a pharmaceutically acceptable carrier.

According to another aspect of the invention, methods of producing a nanoparticle are provided. The methods include (a) preparing a polymer substrate including a biodegradable polymer and at least one antigen; (b) selecting an adjuvant that in cooperation with the antigen is capable of eliciting an immune response in a subject; and (c) encapsulating the selected adjuvant with the polymer substrate to produce the nanoparticle. In certain embodiments, at least a portion of the at least one antigen in the prepared polymer substrate is positioned external to the outer surface of the produced nanoparticle. In some embodiments, at least a portion of the at least one antigen in the prepared polymer substrate is positioned internal to the outer surface of the produced nanoparticle. In some embodiments, the biodegradable polymer is poly(lactic-co-glycolic acid) (PLGA), poly L-lactic acid (PLLA), poly(lactic acid) (PLA), poly(glycolytic acid) (PGA), polycaprolactone, polyglycolide, polylactic acid, poly-3-hydroxybutyrate, polyanhydrides, or hyaluronans. In some embodiments, the diameter of the nanoparticle is less than or equal to 100 nm. In certain embodiments, the diameter of the nanoparticle is between 100 nm and 900 nm. In some embodiments, the adjuvant is a natural or synthetic alphaGalactosylceramide compound or functional variant thereof. In some embodiments, the adjuvant is a CD1d-presented iNKT cell glycolipid agonist. In certain embodiments, the adjuvant is a CD1d-independent iNKT cell agonist. In some embodiments, the CD1d-independent iNKT cell agonist is a Toll-Like Receptor ligand, lipopeptide Pam3Cys-Ser-(Lys)4, or cytosine-guanine dinucleotides (CpG) or a bacterial component (monophosphoryl lipid A, MPLA). In some embodiments, the antigen is derived from a pathogenic bacterial, fungal, parasitic, or viral organism. In certain embodiments, the antigen is derived from an encapsulated bacteria, a *Streptococcus* species, a *Candida* species, a *Cryptococcus* species, a *Brucella* species, a *Salmonella* species, a Staphylococcal species, a *Porphyromonas* species, a *Burkholderia* species, a *Bacillus* species, a Mycobacteria species, a *Shigella* species, a *Pseudomonas* species, a *Bordetella* species, a *Clostridium* species, a Norwalk virus, *Bacillus anthracis, Mycobacterium tuberculosis,* human immunodeficiency virus (HIV), *Chlamydia* species, human Papillomaviruses, Influenza virus, a Paramyxovirus species, Herpes virus, Cytomegalovirus, Varicella-Zoster virus, Epstein-Barr virus, a Hepatitis virus, a *Plasmodium* species, a *Trichomonas* species, a sexually transmitted disease agent, an aerosol-transmitted disease agent, a viral encephalitis disease agent, a protozoan disease agent, a fungal disease agent, a bacterial disease agent, a cancer cell, or a mixture thereof. In some embodiments, the encapsulated bacteria is *Haemophilus* influenza type B, *Streptococcus pneumoniae, Neisseria meningitidis,* Group B *streptococcus* (GBS), *Klebsiella pneumonia, Staphylococcus aureus, Pseudomonas aeruginosa, Burkholderia pseudomallei, Burkholderia mallei, Escherichia coli, Bacteroides fragilis,* or *Salmonella typhi.* In some embodiments, the nanoparticle includes a B-cell population-targeting antigen. In certain embodiments, the B-cell population-targeting antigen includes a polysaccharide, a glycan, an oligonucleotide, a lipopeptide, a protein, a peptide, or a combination of two or more thereof. In some embodiments, the method also includes including a pathogen-derived polysaccharide antigen in the nanoparticle. In some embodiments, the method also includes including at least 2, 3, 4, 5, 6, 7, 8, 9, 10, 25, 50, 60, 70, 80, 90, 100, 125, 150, 175, or 200 different antigens in the polymer substrate. In certain embodiments, the method also includes encapsulating at least 2, 3, 4, 5, 6, 7, 8, 9, or 10 different adjuvants in the polymer substrate. In some embodiments, the produced nanoparticle is not a liposome, does not comprise a lipid bilayer, is not modified on the surface with polyethylene glycol (PEG), and is not associated with a lipid bilayer.

According to another aspect of the invention, nanoparticles are provided that include a polymer substrate, wherein the substrate includes a biodegradable polymer and at least one antigen. In certain embodiments, at least a portion of the at least one antigen is positioned external to the outer surface of the nanoparticle. In some embodiments, at least a portion of the at least one antigen in the polymer substrate is positioned internal to the outer surface of the nanoparticle. In some embodiments, the biodegradable polymer is poly (lactic-co-glycolic acid) (PLGA). In certain embodiments, the nanoparticle has a diameter of less than 100 nm. In some embodiments, the nanoparticle has a diameter between 100 nm and 900 nm. In some embodiments, the antigen is a microbial antigen, a cancer antigen, an autoimmune antigen, or an environmental antigen. In some embodiments, the microbial antigen is a bacterial antigen, a fungal antigen, a parasitic antigen, or a viral antigen. In certain embodiments, the bacterial antigen is an encapsulated bacteria antigen. In some embodiments, the antigen is a Streptococcal antigen, a *Candida* antigen, a *Cryptococcus* antigen, a *Brucella* antigen, a *Salmonella* antigen, a Staphylococcal antigen, a *Porphyromonas* antigen, a *Burkholderia* antigen, a *Bacillus* antigen, a Mycobacteria antigen, a *Shigella* antigen, a *Pseudomonas* antigen, a *Bordetella* antigen, a *Clostridium* antigen, a Norwalk virus antigen, a *Bacillus anthracis* antigen, a *Mycobacterium tuberculosis* antigen, a human immunodeficiency virus (HIV) antigen, a *Chlamydia* antigen, a human Papillomavirus antigen, an Influenza virus antigen, a Paramyxovirus antigen, a Herpes virus antigen, a Cytomegalovirus antigen, a Varicella-Zoster virus antigen, an Epstein-Barr virus antigen, a Hepatitis virus antigen, a *Plasmodium* antigen, a *Trichomonas* antigen, a sexually transmitted disease antigen, an aerosol-transmitted disease antigen, a viral encephalitis disease antigen, a protozoan disease antigen, a fungal disease antigen, a bacterial disease antigen, a tumor antigen, or a cancer antigen. In some embodiments, the encapsulated bacteria is *Haemophilus influenza* type B, *Streptococcus pneumoniae, Neisseria meningitidis*, Group B streptococcus (GBS), *Klebsiella pneumonia, Staphylococcus aureus, Pseudomonas aeruginosa, Burkholderia pseudomallei, Burkholderia mallei, Escherichia coli, Bacteroides fragilis*, or *Salmonella typhi*. In certain embodiments, the nanoparticle also includes a B-cell population-targeting antigen. In some embodiments, the B-cell population-targeting antigen includes a polysaccharide, a glycan, an oligonucleotide, a lipopeptide, a protein, a peptide, or a combination of two or more thereof. In some embodiments, the nanoparticle also includes a pathogen-derived polysaccharide antigen. In certain embodiments, the polymer substrate includes at least 2, 3, 4, 5, 6, 7, 8, 9, 10, 25, 50, 60, 70, 80, 90, 100, 125, 150, 175, or 200 different antigens. In some embodiments, the nanoparticle is not a liposome, does not include a lipid bilayer, is not modified on the surface with polyethylene glycol (PEG), and is not associated with a lipid bilayer.

According to another aspect of the invention, methods of immune stimulation in a subject are provided. The methods include administering to a subject in need of immune stimulation a composition that includes any of the aforementioned nanoparticle embodiments in a dose effective to stimulate in the subject an immune response specific to the nanoparticle's at least one antigen. The invention, in certain aspects also provides methods of treating a disease or condition in a subject, and the methods include administering to a subject in need of such treatment a composition including any embodiment of an aforementioned nanoparticle of the invention, in a dose effective to treat the disease or condition in the subject. In some embodiments of the aforementioned aspects, the dose is effective to prevent or treat a microbial disease or condition, cancer, or an autoimmune disease or condition in the subject. In some embodiments of the aforementioned aspects, the dose is between 1 femtogram and 5 milligrams of antigen. In certain embodiments of the aforementioned aspects, the subject is a human. In some embodiments of the aforementioned aspects, the polymer includes at least one bacterial polysaccharide. In some embodiments of the aforementioned aspects, the method also includes administering one or more additional nanoparticles of any of the aforementioned embodiments of the invention.

According to another aspect of the invention, pharmaceutical compositions are provided that include any of the aforementioned embodiments of a nanoparticle and a pharmaceutically acceptable carrier.

According to another aspect of the invention, methods of producing a nanoparticle are provided. The methods include preparing a polymer substrate that includes a biodegradable polymer and at least one antigen. In certain embodiments, at least a portion of the at least one antigen in the prepared polymer substrate is positioned external to the outer surface of the produced nanoparticle. In some embodiments, at least a portion of the at least one antigen in the prepared polymer substrate is positioned internal to the outer surface of the produced nanoparticle. In some embodiments, the biodegradable polymer is poly(lactic-co-glycolic acid) (PLGA), poly L-lactic acid (PLLA), poly(lactic acid) (PLA), poly (glycolytic acid) (PGA), polycaprolactone, polyglycolide, polylactic acid, poly-3-hydroxybutyrate, polyanhydrides, or hyaluronans. In certain embodiments, the antigen is derived from a pathogenic bacterial, fungal, parasitic, or viral organism. In some embodiments, the antigen is derived from an encapsulated bacteria, a *Streptococcus* species, a *Candida* species, a *Cryptococcus* species, a *Brucella* species, a *Salmonella* species, a Staphylococcal species, a *Porphyromonas* species, a *Burkholderia* species, a *Bacillus* species, a Mycobacteria species, a *Shigella* species, a *Pseudomonas* species, a *Bordetella* species, a *Clostridium* species, a Norwalk virus, *Bacillus anthracis, Mycobacterium tuberculosis*, human immunodeficiency virus (HIV), *Chlamydia* species, human Papillomaviruses, Influenza virus, a Paramyxovirus species, Herpes virus, Cytomegalovirus, Varicella-Zoster virus, Epstein-Barr virus, a Hepatitis virus, a *Plasmodium* species, a *Trichomonas* species, a sexually transmitted disease agent, an aerosol-transmitted disease agent, a viral encephalitis disease agent, a protozoan disease agent, a fungal disease agent, a bacterial disease agent, a cancer cell, or a mixture thereof. In certain embodiments, the encapsulated bacteria is *Haemophilus influenza* type B, *Streptococcus pneumoniae, Neisseria meningitidis*, Group B streptococcus (GBS), *Klebsiella pneumonia, Staphylococcus aureus, Pseudomonas aeruginosa, Burkholderia pseudomallei, Burkholderia mallei, Escherichia coli, Bacteroides fragilis*, or *Salmonella typhi*. In some embodiments, the nanoparticle includes a B-cell population-targeting antigen. In some embodiments, the B-cell population-targeting antigen includes a polysaccharide, a glycan, an oligonucleotide, a lipopeptide, a protein, a peptide, or a combination of two or more thereof. In certain embodiments, the nanoparticle also includes a pathogen-derived polysaccharide antigen in the nanoparticle. In some embodiments, the nanoparticle also includes including at least 2, 3, 4, 5, 6, 7, 8, 9, 10, 25, 50, 60, 70, 80, 90, 100, 125, 150, 175, or 200 different antigens in the polymer substrate. In some embodiments, the produced nanoparticle is not a liposome, does not include a lipid bilayer, is not modified on the surface with polyethylene glycol (PEG), and is not associated with a lipid bilayer.

According to another aspect of the invention, nanoparticles are provided that include a biodegradable polymer and at least one adjuvant in the nanoparticle core. In some embodiments, the biodegradable polymer is poly(lactic-co-glycolic acid) (PLGA). In some embodiments, the nanoparticle has a diameter of less than 100 nm. In certain embodiments, the nanoparticle has a diameter between 100 nm and 900 nm. In some embodiments, the adjuvant is a natural or synthetic alphaGalactosylceramide compound or functional variant thereof. In some embodiments, the adjuvant is a CD1d-presented iNKT cell glycolipid agonist. In certain embodiments, the adjuvant is a CD1d-independent iNKT cell agonist. In some embodiments, the CD1d-independent iNKT cell agonist is a Toll-Like Receptor ligand, an imidazoquinolone compound, lipopeptide Pam3Cys-Ser-(Lys)4, cytosine-guanine dinucleotides (CpG) or a bacterial component (such as monophosphoryl lipid A, MPLA). In some embodiments, the Toll-Like Receptor is Toll-like Receptor 3, 4, 7, or 9. In certain embodiments, the nanoparticle core includes at least 2, 3, 4, 5, 6, 7, 8, 9, or 10 different adjuvants. In some embodiments, the nanoparticle also includes a B-cell population-targeting antigen. In some embodiments, the B-cell population-targeting antigen includes polysaccharide, a glycan, an oligonucleotide, a lipopeptide, a protein, a peptide, or a combination of two or more thereof. In certain embodiments, the nanoparticle is not a liposome, does not include a lipid bilayer, is not modified on the surface with polyethylene glycol (PEG), and is not associated with a lipid bilayer.

According to another aspect of the invention, methods of treating a disease or condition using immune stimulation are provided. The methods include administering to a subject in need of immune stimulation a composition including any of the aforementioned nanoparticle embodiments, in a dose effective to stimulate in the subject an immune response in the subject. The invention, in some aspects also provides methods of treating a disease or condition in a subject, and the methods include administering to a subject in need of such treatment a composition including any embodiment of an aforementioned nanoparticle of the invention, in a dose effective to treat the disease or condition in the subject. In certain embodiments of the aforementioned aspects, the dose is effective to prevent or treat a microbial disease or condition, cancer, or an autoimmune disease or condition in the subject. In some embodiments of the aforementioned aspects, the dose is between 1 femtogram and 5 milligram of adjuvant. In some embodiments of the aforementioned aspects, the adjuvant is a glycolipid adjuvant. In certain embodiments of the aforementioned aspects, the subject is a human. In some embodiments, the adjuvant is a glycolipid adjuvant. In some embodiments of the aforementioned aspects, the nanoparticle also includes a B-cell population-targeting antigen. In certain embodiments of the aforementioned aspects, the B-cell population-targeting antigen includes a polysaccharide, a glycan, an oligonucleotide, a lipopeptide, a protein, a peptide, or a combination of two or more thereof. In some embodiments of the aforementioned aspects, the nanoparticle is administered to the subject in conjunction with at least one additional vaccine. In some embodiments of the aforementioned aspects, the method also includes administering one or more additional nanoparticles of any of the aforementioned embodiments of the invention.

According to another aspect of the invention, pharmaceutical compositions are provided that include any aforementioned embodiments of a nanoparticle and a pharmaceutically acceptable carrier.

According to another aspect of the invention, methods of producing a nanoparticle are provided. The methods include (a) preparing a polymer, (b) selecting an adjuvant; and (c) encapsulating the selected adjuvant with the polymer substrate to produce the nanoparticle. In certain embodiments, the biodegradable polymer is poly(lactic-co-glycolic acid) (PLGA), poly L-lactic acid (PLLA), poly(lactic acid) (PLA), poly(glycolytic acid) (PGA), polycaprolactone, polyglycolide, polylactic acid, poly-3-hydroxybutyrate, polyanhydrides, or hyaluronans. In some embodiments, the diameter of the nanoparticle is less than or equal to 100 nm, or is between 100 nm and 900 nm. In some embodiments, the adjuvant is a natural or synthetic alphaGalactosylceramide compound or functional variant thereof. In certain embodiments, the adjuvant is a CD1d-presented iNKT cell glycolipid agonist. In some embodiments, the adjuvant is a CD1d-independent iNKT cell agonist. In some embodiments, the CD1d-independent iNKT cell agonist is a Toll-Like Receptor ligand, lipopeptide Pam3Cys-Ser-(Lys)4, or cytosine-guanine dinucleotides (CpG) or a bacterial component (such as monophosphoryl lipid A, MPLA). In certain embodiments, the nanoparticle also includes a B-cell population-targeting antigen. In some embodiments, the B-cell population-targeting antigen includes a polysaccharide, a glycan, an oligonucleotide, a lipopeptide, a protein, a peptide, or a combination of two or more thereof. In some embodiments, the method also includes encapsulating at least 2, 3, 4, 5, 6, 7, 8, 9, or 10 different adjuvants in the polymer substrate. In certain embodiments, the produced nanoparticle is not a liposome, does not include a lipid bilayer, is not modified on the surface with polyethylene glycol (PEG), and is not associated with a lipid bilayer.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 2 provides graphs of results indicating PLGA nanoparticles encapsulating αGalCer (αGC-NanoPs) or βGlcCer (βGC-NanoP) activate iNKT cells and B cells in vitro. iNKT and B cells proliferated as signs of activation following three days of in vitro culture with biodegradable PLGA αGC-NanoPs much more efficiently than with soluble αGalCer. Even activation of both iNKT and B cells by the weak agonist, soluble βGlcCer was enhanced by encapsulation of this glycolipid in nanoparticles (βGC-NanoP). Nanoparticles lacking glycolipids were not stimulatory for either iNKT or B cells in this assay (data not shown). Nanoparticles were assessed by Mass Spectrometry and Scanning Electron Microscopy for lipid content and particle size. In the study, spleen cells were isolated, then labeled with carboxyfluorescein diacetate succinimidyl ester (CFSE) and cultured for 3 days with soluble αGalCer, soluble βGlcCer, αGC-NanoPs, or βGC-NanoPs at concentrations of glycolipid noted. FIG. 2B shows % iNKT cell proliferation when treated with Media only, soluble αGC, and αGC containing nanoparticles, which demonstrates that αGalCer encapsulated in nanoparticle form is 1000 fold more potent than soluble αGalCer.

FIG. 3 shows graphs of results of PLGA nanoparticles loaded with αGalCer (αGC-NanoP) and βGlcCer (βGC-NanoP) with or without S. pneumoniae polysaccharide (SpPS) activating iNKT cells in vivo.

FIG. 4 shows graphs of results of in vivo vaccination with glycolipid and polysaccharide containing nanoparticles, demonstrating that the vaccination induced an antigen-specific IgM antibody response. C57BL/6 WT mice immunized once with nanoparticles containing αGalCer and embedded with S. pneumoniae polysaccharides induced robust titers of polysaccharide specific IgM (FIG. 4A), but very little IgG (FIG. 4B). PLGA control nanoparticles induced no S. pneumoniae polysaccharide specific IgG or IgM above background while αGC-PLGA control nanoparticles induced modest polysaccharide-specific IgG and IgM titers. FIG. 4C shows results from the same mice following infection with a lethal dose of systemic S. pneumoniae. Prevnar 13 vaccinated mice served as a positive control, and their survival was significantly enhanced compared to mice receiving only empty nanoparticles (PLGA). At the same time, the αGC-SpPS-NanoP vaccinated mice also showed significantly enhanced survival compared to PLGA only mice. This indicated that the polysaccharide-specific IgM antibody titer induced by NanoP vaccination was sufficient to protect mice against lethal infection (FIG. 4C).

DETAILED DESCRIPTION

Figure 1A:
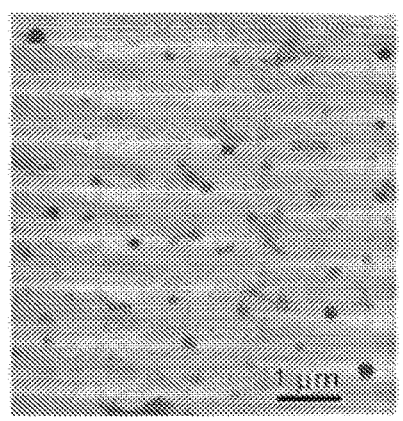
FIG. 1 provides electron micrographic images and a graph demonstrating results of assessment of nanoparticles of the invention. Nanoparticles were synthesized and characterized using electron microscopy. Transmission electron micrograph (TEM) results are shown in FIG. 1A. Results of a nanoparticle size distribution analysis are shown in FIG. 1B, and results of scanning electron micrograph (SEM) analysis of nanoparticles are shown in FIG. 1C.
Figure 1B:
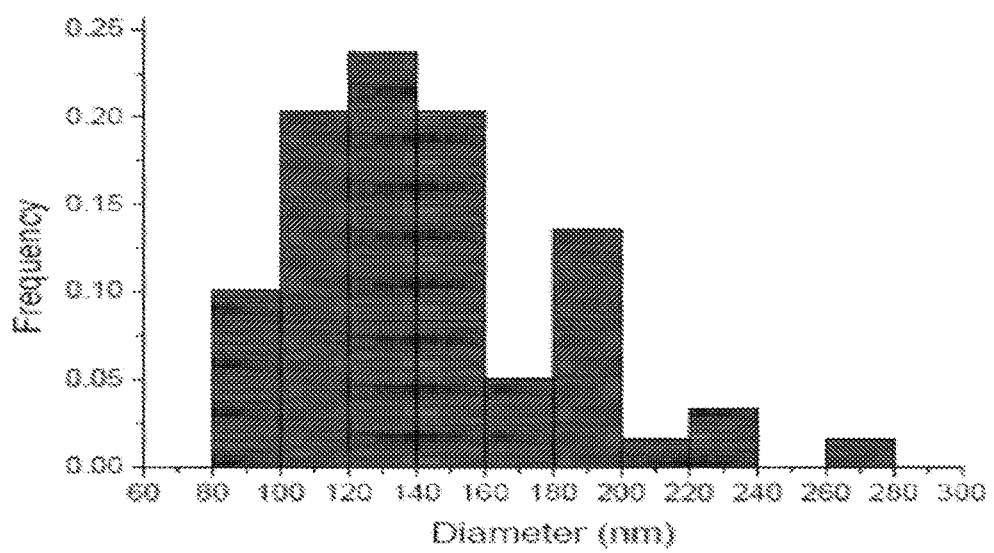

The present invention, in part, relates to nanoparticles and nanoparticle delivery systems. In some embodiments of the invention, a nanoparticle comprises at least three components, an encapsulated adjuvant, a polymer shell, and an embedded antigen (Ag). In certain embodiments of the invention, a nanoparticle comprises a polymer shell and an encapsulated adjuvant. In certain embodiments of the invention, a nanoparticle comprises a polymer shell with embedded antigen. The invention, in part also provides nanoparticle compositions, nanoparticle vaccines, methods of nanoparticle synthesis, and methods of use of the nanoparticle for immune stimulation. Some nanoparticles of the invention may have surface embedded and/or exposed antigen targets, which assist in directing the nanoparticles to antigen-specific B cells in order to facilitate a B cell response. In some embodiments of the invention, nanoparticles can be prepared that include at least one adjuvant that activates iNKT cells, and at least one antigen that is recognized by B cells. Nanoparticles of the invention can be administered to a subject as a vaccine that efficiently directs iNKT cell help to antigen-specific B cells that have engaged nanoparticles in order to produce a combined humoral and cellular immune response against a variety of pathogens. In part, the invention provides nanoparticle vaccines that when administered to a subject are useful to efficiently direct iNKT cell help to antigen-specific B cells that have engulfed administered nanoparticles.

Vaccination methods have now been described that propose to circumvent anergy and safely and efficiently stimulate an immune response. It has been suggested that co-administration of a pathogen-derived B cell antigen (polysaccharide) in combination with αGalCer, results in iNKT activation in the context of B cell receptor (BCR) crosslinking and upregulated expression of co-stimulatory molecules by B cells. Thus, some embodiments of the invention include preparation and administration of nanoparticles embedded with a B cell antigen to initiate crosslinking of the BCR in the context of αGalCer presentation, thereby overcoming the problem of B cell induced anergy and facilitating antigen-specific antibody production. A nanoparticle vaccine of the invention may include, in part, a nanoparticle composed of a polymer substrate, wherein the polymer substrate comprises a biodegradable polymer and at least one antigen and the nanoparticle further comprises at least one adjuvant in the nanoparticle's core. In certain embodiments of the invention, a nanoparticle vaccine of the invention may include, in part, a nanoparticle composed of a polymer substrate, wherein the polymer substrate comprises a biodegradable polymer and at least one antigen. Other embodiments of the invention include a nanoparticle vaccine that includes a nanoparticle composed of a polymer substrate and at least one adjuvant in the nanoparticle's core. The nanoparticles (e.g., nanoparticle vaccines) of the invention can be administered to a subject resulting in an efficient stimulation of a protective immune response in the subject.

Nanoparticles

The invention provides, in part, nanoparticles suitable for immune stimulation in subjects. Nanoparticles of the invention may be used to deliver antigens and adjuvants, just antigens, or just adjuvants, in a manner resulting in an enhanced immune response. The at least one antigen and at least one adjuvant in a nanoparticle of the invention may act cooperatively to elicit an immune response in a subject to whom the nanoparticle is administered. A nanoparticle of the invention is composed of, in part, a polymer substrate and the nanoparticle has a core. A nanoparticle of the invention may also include, in some embodiments, at least one antigen and at least one adjuvant, wherein the adjuvant is positioned in the nanoparticle core. The term "core", as used herein in reference to nanoparticles of the invention, means the portion of the nanoparticle that is internal to the polymer substrate of the nanoparticle. In some embodiments of the invention, the nanoparticle core contains one or more adjuvants and in certain embodiments of the invention, the core of a nanoparticle does not contain any adjuvant. It will be understood that the core of a nanoparticle of the invention may, in addition to one or more adjuvants, or in the absence of any adjuvants, include a medium, such as for example, an aqueous or non-aqueous carrier medium. Examples of media that may be positioned in the core of a nanoparticle of some embodiments of the invention include, but are not limited to an aqueous medium, a non-aqueous medium, etc. Examples of media that may be used in nanoparticles of the invention include, but are not limited to phosphate buffered saline (PBS) and 0.9% NaCl.

A nanoparticle of the invention comprises a polymer substrate, which in some embodiments of the invention, comprises a biodegradable polymer and one or more antigens. Antigens included in a nanoparticle of the invention may be incorporated into the polymer substrate. As used herein, the term "incorporated", with respect to antigens and the polymer substrate, means the antigen is integrated into the polymer that makes up part of the polymer substrate. For example, unlike prior liposome or nanoparticle vaccines in which an antigen may be attached to the outer surface of a vaccine particle (nanoparticle or liposome), in a nanoparticle of the invention that includes one or more antigens, the one or more antigens may be integrated into the polymer substrate when the nanoparticle is prepared, and thus the antigen molecules are intercalated with the polymer molecules in the substrate and the polymer and antigen together form the polymer substrate.

The invention, in some aspects includes incorporating one or more antigens into a polymer of a nanoparticle. In some instances, an antigen molecule incorporated into the polymer of a nanoparticle may be positioned such that the antigen molecule is fully internal to the nanoparticle surface at the time of its production. Use of a biodegradable polymer in a nanoparticle of the invention that includes one or more antigens, may result in at least a portion of an antigen being positioned internal to the outer surface of the nanoparticle at the time of the nanoparticle's production becoming positioned external to the outer surface of the nanoparticle as the polymer degrades. Thus, biodegradation of a nanoparticle of the invention that includes one or more antigens may result in the change in position of at least a portion of an antigen from fully internal to the nanoparticle to being positioned, at least in part, external to the outer surface of the remainder of the nanoparticle. As used herein, the term "remainder" in reference to a nanoparticle of the invention, means the portion of the nanoparticle that exists after the onset of polymer biodegradation in the nanoparticle.

The invention, in part, also encompasses nanoparticles with at least a portion of an antigen incorporated in a polymer being positioned external to the outer surface of the nanoparticle at the time of the nanoparticle's production. In certain embodiments of the invention, a nanoparticle includes a polymer substrate in which at least one antigen is positioned such that at least a portion of the antigen is external to the outer surface of the nanoparticle. As used herein, the phrase "at least a portion" means at least 5%, 10%, 15%, 20%, 25%, 30%, 35%, 40%, 45%, 50%, 55%, 60%, 65%, 70%, 75%, 80%, 85%, 90%, 95%, or 99%, but less than 100% of the antigen. In some embodiments of the invention, at least a portion of an antigen is positioned internal to the outer surface of the nanoparticle and in certain embodiments of the invention 100% of an antigen is positioned internal to the outer surface of the nanoparticle. Biodegradation of a polymer of a nanoparticle of the invention that includes one or more antigens may result in the release of the one or more antigens from the nanoparticle, which means that 100% of the antigen is external to the outer surface of the nanoparticle. It will be understood that degradation of the biodegradable polymer will result in a decrease in the portion of an antigen that is positioned internal to the outer surface of the nanoparticle. Thus, after administration to a subject, degradation of an administered nanoparticle of the invention will result in increasing exposure of antigen within the environment of the subject.

With respect to positioning, adjuvants that are included in nanoparticles of the invention are positioned within the nanoparticle core, and thus at the time of production of the nanoparticle that includes one or more adjuvants, an adjuvant molecule is positioned fully internal to the outer surface of the produced nanoparticle. With biodegradation of a nanoparticle polymer, one or more portions of the previously internal adjuvant molecule may become positioned external to the outer surface of the remainder of the nanoparticle and/or may be released from the nanoparticle. Thus, biodegradation of a polymer of a nanoparticle of the invention that includes one or more adjuvants may result in the release of the one or more adjuvants from the nanoparticle as degradation of the administered nanoparticle of the invention results in increasing exposure and release into the subject of adjuvant that was previously contained within the nanoparticle core. In certain embodiments of nanoparticles of the invention that include one or more antigens and include one or more adjuvants, biodegradation of a polymer of the nanoparticle results in an increasing exposure and release into the subject of antigen and adjuvant that were contained in the nanoparticle.

A nanoparticle of the invention is not a liposome, which is recognized in the art as including a lipid outer layer with a void volume and/or a fluid volume at its core. A nanoparticle of the invention neither includes, nor is it associated with a lipid bilayer. As used herein, the term "associated with" when used in referent to a lipid bilayer means attached to, connected to, covered with, conjugated to, and the like. Thus, a nanoparticle of the invention is not attached to, connected to, covered with, or conjugated to a lipid bilayer. A nanoparticle of the invention does not have a lipid bilayer coating and antigens and adjuvants that are incorporated into nanoparticles of the invention are not incorporated into the nanoparticles by attachment to, or integration into a lipid bilayer. Unlike alternative delivery particles such as "stealth" particles, which are known in the art to be externally coated with compounds having properties that allow the particles to evade clearance by the body and remain in circulation for extended periods of time. (See for example Jokerst, J. V., et. al., 2011, *Nanomedicine* 6(4): 715-728 and US Patent Publication No. 20110229556), a nanoparticle of the invention is not modified on its external surface with such compounds. Examples of compounds that are not included on the external surface of nanoparticles of the invention, include, but are not limited to, compounds such as polyethylene glycol (PEG), chitosan, chitosan-thioglycolic acid, mucin etc. Additional "stealth" coatings are known in the art and are not included on nanoparticles of the invention.

In some embodiments of the invention, a nanoparticle may have an average diameter that is less than 100 nanometer (nm), or between 100 nm and 900 nm. In certain embodiments of the invention a nanoparticle may have an average diameter in the range of 1 nm to 20 nm, 1 nm to 40 nm, 1 nm to 60 nm, 1 nm to 80 nm, 1 nm to 100 nm, 50 nm to 100 nm, 50 nm to 200 nm, 50 nm to 300 nm, 50 nm to 400 nm, 50 nm to 500 nm, 50 nm to 600 nm 50 nm to 700 nm, 50 nm to 800 nm, 50 nm to 900 nm, 50 nm to 1000 nm, 100 nm to 200 nm, 100 nm to 300 nm, 100 nm to 400 nm, 100 nm to 500 nm, 100 nm to 600 nm, 100 nm to 700 nm, 100 nm to 800 nm, 100 nm to 900 nm, or 100 nm to 1000 nm.

Nanoparticles of the invention may be of any shape and are not limited to a perfectly spherical shape. As an example, they may be elliptical, oval, or oblong. Nanoparticle size as set forth herein, refers to an average diameter of a nanoparticle of the invention. As used herein, the term "average diameter" refers to the average of two or more diameter measurements of a nanoparticle. The dimensions of the particles may also be expressed in terms of the longest diameter or cross-section.

A nanoparticle of the invention may be isolated, which, as used herein means a nanoparticle that is physically separated in whole or in part from the environment in which it was synthesized. Separation may occur based on weight (or mass), density (including buoyant density), size, color, and the like, etc. Moreover, nanoparticles of the invention may be isolated using an art-known means such as, but not limited to, centrifugation, filtration, etc. As used herein, the term "nanoparticle vaccine" used in reference to a vaccine of the invention, comprises a plurality of nanoparticles of the invention.

In embodiments of the invention, nanoparticles are not conjugated to cells and are not administered with cells to a subject. Nanoparticles of the invention may be administered alone or with other agents, typically in a pharmaceutically acceptable carrier. Nanoparticles of the invention may or may not comprise one or more of a targeting agent and a detectable label. Nanoparticles of the invention may also be produced that include one or more additional therapeutic agents that may be released during nanoparticle biodegradation.

A nanoparticle of the invention may also be administered to a subject at the same time as, or prior to, or subsequent to administration of another vaccine that is a different nanoparticle vaccine of the invention or another vaccine that is not a nanoparticle vaccine of the invention. Such administrations of more than one vaccine, wherein at least one of the more than one vaccine is a nanoparticle vaccine of the invention, may result in an additive effect of the vaccines in the subject and thus enhance the vaccine effectiveness in the subject. Also, in certain embodiments, administrations of more than one vaccine, wherein at least one of the more than one vaccine is a nanoparticle vaccine of the invention, may result in an synergistic effect of the vaccines in the subject, such that the vaccine effect is more than the additive effect of the administered vaccines administered in the absence of the other one or more vaccines.

In certain embodiments of the invention, a nanoparticle may be produced that includes at least 1, 2, 3, 4, 5, 6, 7, 8, 9, 10, 20, 30, 40, 50, 60, 70, 80, 90, or more antigens as described herein but that does not include any adjuvants in the nanoparticle. Such an adjuvant-free nanoparticle of the invention may be administered in a nanoparticle vaccine to a subject at the same time as, or prior to, or subsequent to administration of another vaccine that is a different nanoparticle vaccine of the invention (e.g., a nanoparticle vaccine that includes nanoparticles comprising one or more adjuvants) or another vaccine that is not a nanoparticle vaccine of the invention. Such administrations of more than one vaccine, wherein at least one of the more than one vaccine is a nanoparticle vaccine of the invention that does not include an adjuvant, may result in an additive effect of the vaccines or a synergistic effect of the vaccines.

In certain embodiments of the invention, a nanoparticle may be produced that includes at least 1, 2, 3, 4, 5, 6, 7, 8, 9, 10, 20, 30, 40, 50, 60, 70, 80, 90, or more adjuvants as described herein but that does not include any antigens in the nanoparticle. Such an antigen-free nanoparticle of the invention may be administered in a nanoparticle vaccine to a subject at the same time as, or prior to, or subsequent to administration of another vaccine that is a different nanoparticle vaccine of the invention (e.g., a nanoparticle vaccine that includes nanoparticles comprising one or more antigens) or another vaccine that is not a nanoparticle vaccine of the invention. Such administrations of more than one vaccine, wherein at least one of the more than one vaccine is a nanoparticle vaccine of the invention that does not include an antigen, may result in an additive effect of the vaccines or a synergistic effect of the vaccines.

Polymers

Biodegradable polymers that may be used in nanoparticles of the invention may be natural or synthetic polymers. Biodegradable polymers used in certain embodiments of nanoparticles of the invention include but are not limited to poly(lactic-co-glycolic acid) (PLGA); poly L-lactic acid (PLLA); poly(lactic acid) (PLA); poly(glycolytic acid) (PGA); polycaprolactone; polyglycolide; polylactic acid; poly-3-hydroxybutyrate; polyanhydrides; hyaluronans; poly (D-lactic acid) (PDLA); poly (D,L-lactic acid) (PDLLA); meso-poly (lactic acid); polyhydroxyalkanoates, including but not limited to poly (3-hydroxybutyrate) (PHB), 3-hydroxyvalerate, poly(dioxanone), and poly (caprolactone); polyethers, including but not limited to polycaprolactone (PCL), and poly (propylene fumarate) (PPF); polyanhydrides, including but not limited to aliphatic-homo-polyanhydrosides, poly (sebacic anhydride) (PSA), hydrophobic aromatic diacid monomers, aliphatic fatty acid dimers (PAD), and 1,8-bis-(p-carboxyphenoxy)-3,6-dioxaoctane; polyacetals including but not limited to polyketals; poly (ortho esters) including but not limited to POE IV; polycarbonates, including but not limited to poly(trimethylene carbonate) (PTMC), dihydroxacetone (DHA), poly (desaminotyrosyl-tyrosine alkyl ester carbonates) (PDTE); polyphosphazenes; and polyphosphoesters, including but not limited to polyphosphonates and polyphosphates. Additional art-known biodegradable polymers may also be used in nanoparticles of the invention. (See Ulery, B. et. al., *J Polym Sci B Polym Phys*. 2011 Jun. 15; 49(12): 832-864) A nanoparticle of the invention may include a single type of polymer, or may, in certain embodiments, include a mixture of at least 2, 3, 4, 5, 6, 7, 8, 9, 10, 11, 12, 13, 14, 15, 16, 17, 18, 19, 20 or more different types of polymers.

Antigens

In certain embodiments of the invention, a nanoparticle may include one or more antigens. The term "antigen" as used herein means an agent that elicits (e.g., stimulates) an immune response in a subject. A nanoparticle of the invention may include zero antigens or may include at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 200, 400, 500 or more different antigens, including all integers in between. Thus, in certain embodiments of the invention, a nanoparticle of the invention may include a single type of antigen, or combinations of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 200 or more (including all integers in between) different antigens. In certain embodiments of nanoparticles of the invention the number of different antigens combined in the nanoparticle may be between 2 and 5, 2 and 10, 2 and 25, 2 and 50, 2 and 75, 2 and 100, 2 and 125, 2 and 150, 2 and 175, 2 and 200, 2 and 500, 10 and 25, 10 and 50, 10 and 100, 10 and 150, 10 and 200, 50 and 75, 50 and 100, 50 and 150, 50 and 200, 100 and 200, 150 and 200, 150 and 500, or 200 and 500.

Selection of antigens for inclusion in a nanoparticle of the invention can be based, at least in part, on the type of immune stimulation desired, the health condition of a subject to receive a nanoparticle of the invention, etc. In a non-limiting example, a nanoparticle of the invention useful to treat a bacterial infection may include an antigen derived from the bacterial strain to be treated, and such an antigen may be selected. Thus, for administration to a subject to treat a pathogenic disease or condition, combinations of antigens for inclusion in a nanoparticle may be selected, at least in part, to target one or more different strains of a single pathogen, one or more different pathogens, a combination of targeting multiple strains of a single pathogen and multiple different pathogens, etc. Similarly, for treatment of cancer, a single cancer antigen may be selected or 2, 3, 4, 5, 6, 7, or more different cancer antigens from one or more different cancers may be selection for inclusions in a nanoparticle of the invention. Examples of antigen types that may be included in a nanoparticle of the invention, include, but are not limited to, microbial antigens, cancer antigens, autoimmune antigens, or environmental antigens. An antigen included in a nanoparticle of the invention may comprise a natural or synthetic peptide, lipid, glycolipid, lipopeptide, or carbohydrate molecule.

In some embodiments of the invention, a nanoparticle may include one or more antigens where the antigen is a pathogenic antigen. As used herein the term "pathogenic" means a bacterium, virus, fungi, or other microorganism that can cause disease. In certain embodiments of the invention, a pathogenic antigen may be a microbial antigen. Examples of microbial antigens include, but are not limited to, bacterial antigens, fungal antigens, parasitic antigens, or viral antigens.

In some aspects of the invention, a bacterial antigen is an encapsulated bacterial antigen. Examples of encapsulated bacterial antigens that may be used in nanoparticles of the invention, include, but are not limited to *Haemophilus influenza* type B antigen, *Streptococcus pneumonia* antigen, *Neisseria meningitides* antigen, Group B *streptococcus* (GBS) antigen, *Klebsiella pneumonia* antigen, *Staphylococcus aureus* antigen, *Pseudomonas aeruginosa* antigen, *Burkholderia pseudomallei* antigen, *Burkholderia mallei* antigen, *Escherichia coli*, *Bacteroides fragilis* antigen, and *Salmonella typhi* antigen.

Non-limiting examples of antigens that may be used in a nanoparticles of the invention, include or may be derived from: a Streptococcal antigen, a *Candida* antigen, a *Cryptococcus* antigen, a *Brucella* antigen, a *Salmonella* antigen, a Staphylococcal antigen, a *Porphyromonas* antigen, a *Burkholderia* antigen, a *Bacillus* antigen, a Mycobacteria antigen, a *Shigella* antigen, a *Pseudomonas* antigen, a *Bordetella* antigen, a *Clostridium* antigen, a Norwalk virus antigen, a *Bacillus anthracis* antigen, a *Mycobacterium tuberculosis* antigen, a human immunodeficiency virus (HIV) antigen, a *Chlamydia* antigen, a human Papillomavirus antigen, an Influenza virus antigen, a Paramyxovirus antigen, a Herpes virus antigen, a Cytomegalovirus antigen, a Varicella-Zoster virus antigen, an Epstein-Barr virus antigen, a Hepatitis virus antigen, a *Plasmodium* antigen, a *Trichomonas* antigen, a sexually transmitted disease antigen, an aerosol-transmitted disease antigen, a viral encephalitis disease antigen, a protozoan disease antigen, a fungal disease antigen, a bacterial disease antigen, a tumor antigen, or a cancer antigen.

In certain embodiments, a nanoparticle of the invention may include a B-cell population-targeting antigen. Non-limiting examples of a B-cell population-targeting antigen are antigens that comprise 1, 2, 3, 4, 5, 6, or more of a polysaccharide, a glycan, an oligonucleotide, a lipopeptide, a protein, hapten, or a peptide. B-cell population targeting antigens are known in the art. A B cell targeting antigen is an antigen that is recognized and/or engaged by one or more antigen-specific B cells. (See Janeway's Immunology, 8th Edition, K. M. Murphy, Garland Science; Aug. 20, 2012). A compound that is detectable by a B cell may serve as, and be considered to be a B-cell antigen. In certain embodiments of the invention, a B-cell targeting antigen targets one or more B-cell populations.

A nanoparticle of the invention may, in some embodiments, include a polysaccharide antigen that is derived from a pathogen, and may be a naturally occurring antigen. As used herein, the term "derived from" with respect to the origination of an antigen, means the antigen originates from a source such as a cancer cell, microbial organism, pollutant, subject cell, etc. In certain embodiments of the invention an antigen may be a naturally occurring antigen that is modified to increase antigenicity, half-life (e.g., resistance to degradation), delivery, targeting, etc. Thus, an antigen included in a nanoparticle of the invention may be a naturally occurring antigen or a modified antigen, which may also be referred to herein as a functional variant of an antigen. As used herein the term "functional variant" used in reference to an antigen, means an antigen compound that is modified from a natural or synthetic antigen, and that retains at least some or all of the antigen functionality of the unmodified antigen. An example of a naturally occurring antigen, though not intended to be limiting, is a polysaccharide from *Streptococcus pneumoniae* as shown in data presented herein. A modified antigen may be a compound or molecule that has been artificially synthesized, a non-limiting example of which may be a glycolipid or an oligonucleotide. Although oligonucleotides may be utilized as adjuvants, oligonucleotides may also be used as antigens. Oligonucleotides useful in the invention may be natural or artificially synthesized and may, in some embodiments of the invention be synthesized and include a non-naturally occurring phosphorothioate backbone, which may increase stability. [See, for example, Krieg, A M; et al., 1995, *Nature* 374 (6522): 546-9 and Vollmer, J; & Krieg, A M, 2009, *Advanced drug delivery reviews* 61 (3): 195-204]. Additional examples of modified antigens are known in the art and may be used in certain embodiments of the invention.

Non-limiting examples of antigens that may be used in embodiments of nanoparticles of the invention include, but are not limited to microbial antigens that are derived from microbial species such as without limitation bacterial, viral, fungal, parasitic, and mycobacterial species. Thus, a microbial antigen may be a naturally occurring bacterial antigen, viral antigen, fungal antigen, parasitic antigen, or mycobacterial antigen or modified derivative thereof. Non-limiting examples of bacterial, viral, fungal, parasitic, and mycobacterial species are provided herein. The microbial antigen may be part of a microbial species or it may be the entire microbe, and may be a naturally occurring antigen, a synthetic antigen, or an antigen derived from a natural antigen e.g., a modified antigen.

Examples of species from which a bacterial antigen may be obtained or derived, although not intended to be limiting, include *E. coli*, Staphylococcal, Streptococcal, *Pseudomonas*, *Clostridium difficile*, *Legionella*, *Pneumococcus*, *Haemophilus*, *Klebsiella*, *Enterobacter*, *Citrobacter*, *Neisseria*, *Shigella*, *Salmonella*, *Listeria*, *Pasteurella*, *Streptobacillus*, *Spirillum*, *Treponema*, *Actinomyces*, *Borrelia*, *Corynebacterium*, *Nocardia*, *Gardnerella*, *Campylobacter*, *Spirochaeta*, *Proteus*, *Bacteroides*, *H. pylori*, and anthrax, etc.

Examples of species from which a viral antigen may be obtained or derived, although not intended to be limiting, include HIV, Herpes simplex virus 1, Herpes simplex virus 2, cytomegalovirus, hepatitis A virus, hepatitis B virus, hepatitis C virus, human papilloma virus, Epstein Barr virus, rotavirus, adenovirus, influenza A virus, respiratory syncytial virus, varicella-zoster virus, small pox, monkey pox, or SARS, etc.

Examples of species from which a fungal antigen may be obtained or derived, although not intended to be limiting, include candidiasis, ringworm, histoplasmosis, blastomycosis, paracoccidioidomycosis, crytococcosis, aspergillosis, chromomycosis, mycetoma infections, pseudallescheriasis, or tinea versicolor infection, etc.

Examples of species from which a parasitic antigen may be obtained or derived, although not intended to be limiting, include amebiasis, *Trypanosoma cruzi*, Fascioliasis, Leishmaniasis, *Plasmodium*, Onchocerciasis, Paragonimiasis, *Trypanosoma brucei, Pneumocystis, Trichomonas vaginalis, Taenia, Hymenolepsis, Echinococcus, Schistosomiasis, neurocysticercosis, Necator americanus*, or *Trichuris trichiura*, etc.

Examples of species from which a mycobacterial antigen may be obtained or derived, although not intended to be limiting, include *M. tuberculosis* or *M. leprae*, etc.

Nanoparticles and methods of nanoparticle use herein also include, in some embodiments, one or more cancer antigens. A cancer antigen is an antigen that is expressed at higher levels in cancer cells than in non-cancer cells. Such an antigen may be a "marker" for a cancer cell in that it is recognized as its presence being characteristic of the presence of a cancer. A cancer antigen may be expressed within a cancer cell or on the surface of the cancer cell. Additional art-known cancer antigens may be used in nanoparticles and methods of the invention. (See Cheever, M. A. et al., *Clin Cancer Res* 2009; 15:5323-5337).

In certain embodiments of the invention, a nanoparticle of the invention may include 1 or more antigens and may include no adjuvants, and be referred to as an "adjuvant-free" nanoparticle of the invention. Some aspects of the invention may include administration of an adjuvant-free nanoparticle vaccine of the invention as a treatment for a disease or condition. In certain embodiments of the invention, an adjuvant-free nanoparticle vaccine may be administered in conjunction with one or more adjuvant-containing nanoparticle vaccines of the invention, and may enhance the efficacy of the one or more adjuvant-containing nanoparticle vaccines. In some embodiments of the invention, an adjuvant-free nanoparticle vaccine of the invention may be administered to a subject in conjunction with one or more other vaccines that are not nanoparticle vaccines of the invention, and may enhance the efficacy of the other vaccines. As used herein, administration in conjunction with another vaccine may include co-administration of the vaccines at the same time, or one vaccine administered prior to or after another vaccine.

Adjuvants

In certain embodiments of the invention, a nanoparticle of the invention may include one or more adjuvants. The term "adjuvant" as used herein means an agent that enhances an immune response elicited by an antigen in a subject. Thus, the one or more adjuvants that are included in a nanoparticle of the invention may, upon administration of the nanoparticle to a subject, increase the immune response that is stimulated in the subject by the one or more antigens included in the nanoparticle. An adjuvant in a nanoparticle of the invention that does not include an antigen may, upon administration to a subject, increase the immune response stimulated in the subject by another vaccine or antigen that was not administered to the subject as part of the nanoparticle. The at least one antigen and at least one adjuvant in a nanoparticle of the invention may act cooperatively, (e.g., function in conjunction with each other), to elicit a stronger immune response in a subject to whom the nanoparticle is administered, than would result if the antigen were administered in the absence of the adjuvant. In embodiments of the invention, a nanoparticle may include zero adjuvants or may include 1, 2, 3, 4, 5, 6, 7, 8, 9, 10, 20, 30, 40, 50, 60, 70, 80, 90, 100, 150, 200 or more different antigens and may include a single type of adjuvant, or a combination of 2, 3, 4, 5, 6, 7, 8, 9, 10, 20, 30, 40, 50, or more different adjuvants. Selection of one or more adjuvants for inclusion in a nanoparticle of the invention may be based on the type of immune stimulation desired, condition of a subject to be administered the nanoparticle, etc. Combinations of adjuvants for inclusion in some nanoparticles of the invention may be selected to enhance one or more antigens to one or more microbial strains, cancer cell types, etc. A nanoparticle of the invention may, in some embodiments, include an adjuvant that is modified to increase its efficacy, half-life (e.g., resistance to degradation), etc. A non-limiting example of a possible pairing of adjuvant with antigen in an embodiment of a nanoparticle of the invention is inclusion of alphaGalCer as an adjuvant and one serotype or a combination of from 2 to 90 different serotypes of serotype 3 *S. pneumoniae* polysaccharides as antigen(s). An additional non-limiting example of an adjuvant/antigen combination in an embodiment of a nanoparticle of the invention is inclusion of a CpG oligosaccharide adjuvant (optionally having a modified phosphorothioate backbone) and inclusion of one or a combination between 2 and 90 serotypes of serotype 3 *S. pneumoniae* polysaccharides as antigen(s). The invention contemplates numerous different combinations and pairing of antigens and adjuvants for inclusion in embodiments of nanoparticles of the invention.

In certain embodiments of the invention, a nanoparticle of the invention may include 1 or more adjuvants and may include no antigens, and be referred to as an "adjuvant-only" nanoparticle of the invention. Examples of results obtained with adjuvant-only nanoparticles of the invention are shown in FIG. 2. Some aspects of the invention may include administration of an adjuvant-only nanoparticle vaccine of the invention as a treatment for a disease or condition. In certain embodiments of the invention, an adjuvant-only nanoparticle vaccine may be administered in conjunction with one or more antigen-containing nanoparticle vaccines of the invention, and may enhance the efficacy of the one or more antigen-containing nanoparticle vaccines. In some embodiments of the invention, an adjuvant-only nanoparticle vaccine of the invention may be administered to a subject in conjunction with one or more other vaccines that are not nanoparticle vaccines of the invention, and may enhance the efficacy of the other vaccines. As used herein, administration in conjunction with another vaccine may include co-administration of the vaccines at the same time, or one vaccine administered prior to or after another vaccine. In an adjuvant-only nanoparticle of the invention, the adjuvant may be in the core of the polymer with no polysaccharide or other antigen mixed into the polymer. One or more adjuvant-only nanoparticle vaccines of the invention may be administered to a subject in conjunction with another vaccine and may enhance the activity of the other vaccine and enhance the immune response generated by the other vaccine.

An adjuvant that may be included in the core of a nanoparticle of the invention may be a natural or synthetic adjuvant and may be a glycolipid adjuvant or a non-glycolipid adjuvant. A non-limiting example of a glycolipid adjuvant may be an alpha-galactosylceramide (alphaGalCer, which is also referred to herein as αGalCer) compound or functional variant. As used herein the term "functional variant" used in reference to an adjuvant, means an adjuvant compound that is modified from a natural or synthetic adjuvant, and retains at least some or all of the adjuvant functionality of the unmodified adjuvant. In an instance wherein an included adjuvant is a glycolipid, the nanoparticle core may include the glycolipid adjuvant that is in the form of a micell. In a micell formation, the one or more glycolipid adjuvants may form a glycolipid "ball" having the sugar heads in the center with the glycolipid fatty acid tails pointing outward. The nanoparticle polymer substrate may encapsulate such a micell.

In certain nanoparticle embodiments, one or more adjuvants that are not glycolipids may be contained in the core of the nanoparticle. It will be understood that the core of a nanoparticle of the invention may, in addition to one or more adjuvants, also include a medium, such as for example, an aqueous or non-aqueous carrier medium. It will be understood that certain embodiments of a nanoparticle of the invention may include one or more of glycolipid adjuvants, one or more non-glypolipid adjuvants, or a combination of one or more glycolipid and non-glycolipid adjuvants.

In some embodiments of the invention, an adjuvant that is included in a nanoparticle is a natural or synthetic alpha-galactosylceramide (alphaGalCer) compound or functional variant thereof. In certain embodiments, nanoparticles of the invention may include an adjuvant that is a CD1d-presented iNKT cell glycolipid agonist. In other embodiments, a nanoparticle of the invention may include an adjuvant that is a CD1d-independent iNKT cell agonist. Examples of CD1d-independent iNKT cell agonists that may be included in an nanoparticle of the invention include, but are not limited to, a Toll-Like Receptor ligand, an imidazoquinolone compound, lipopeptide Pam3Cys-Ser-(Lys)4, a cytosine-guanine dinucleotide (CpG), or a bacterial component such as, but not limited to, monophosphoryl lipid A, (MPLA). In certain embodiments of the invention, the Toll-Like Receptor is Toll-like Receptor 3, 4, 7, or 9. The identification and use of different adjuvants is well known in the art, including as a non-limiting example, in methods of using TLR ligands to activate B cells. (See U.S. Patent Publication No. 20050106142).

Additional examples of adjuvants that may be included in embodiments of nanoparticles of the invention, include, but are not limited to DNA molecules; RNA molecules; oligodeoxynucleotide molecules, for example, CpG DNA; small molecules; phosphorothioate-containing molecules such as phosphorothioate nucleotide analogs and nucleic acids containing phosphorothioate backbone linkages, or other art-known adjuvant molecules. [See for example, Phee et. al., Clin Exp Vaccine Res 2012 Vol. 1(1):50-63; Badiee et. al., Vaccine 2013 Jan. 21; Vol. 31(5):735-49; and Hawken et. al. Vaccine 2012 Nov. 19; 30(49): 6971-9].

Subjects

The invention, in part, pertains to eliciting an immune response to treat a subject in need of immune stimulation. Nanoparticle vaccines, compositions, and methods of the invention, comprise a plurality of at least one nanoparticle of the invention, and may be used to stimulate an immune response to prevent or treat a disease or condition in a subject having, or at risk of having, the disease or condition. Examples of diseases or conditions that may be treated or prevented by immune stimulation by nanoparticles of the invention include, but are not limited to: an infection, an auto-immune response, a cancer, tissue or organ rejection, etc. The presence of or risk of having a disease or condition in a subject may be determined using standard diagnostic means, known and routinely practiced in the medical and veterinary arts. The selection of antigens, adjuvants, and combinations thereof to stimulate a subject's immune system to prevent or treat a disease or condition in the subject and methods of monitoring a disease or condition in a subject are routinely practiced in the medical and veterinary arts.

As used herein, a subject shall mean a human or vertebrate mammal including but not limited to a dog, cat, horse, cow, goat, and primate, e.g., monkey. Thus, the invention can be used to treat diseases or conditions in human and non-human (animal) subjects. For instance, methods and compositions of the invention can be used in veterinary or livestock applications as well as in human prevention and treatment regimens. In addition, nanoparticle vaccines and methods of the invention may be used to treat wild (e.g., non-domesticated) animal subjects such as bison, elk, deer, raccoons, lions, bears, moose, etc. In some embodiments of the invention, the subject is a human.

Non-limiting examples of subjects to which the present methods and nanoparticle vaccines of the invention can be applied are subjects who are diagnosed with, suspected of having, or at risk of having, a disease or condition that may be treated by administering a vaccine to stimulate an immune response. Methods of the invention may be applied to a subject who, at the time of treatment, has been diagnosed as having a disease or condition, or a subject who is considered to be at risk for having or developing the disease or condition.

In some aspects of the invention, a subject having a disease or condition, may be a subject who has sufficient symptoms of the disease or condition to be considered suitable for treatment with nanoparticle vaccine of the invention, or may be a subject who has been diagnosed with, and so has been confirmed to have the disease or condition. Examples of symptoms that may indicate a disease or condition that may be suitable a treatment to stimulate an immune response are known by those of skill in the art, and may include, but are not limited to fever, increased white blood count, diarrhea, malnutrition, etc.

In some aspects of the invention, a subject is at risk of having or developing a disease or condition that may be treated with a nanoparticle vaccine of the invention. A subject at risk of developing such a disease or condition is one who has an increased probability of developing the disease or condition, compared to a control risk of developing the disease or condition. In some embodiments of the invention, a level of risk may be statistically significant compared to a control level of risk. A subject at risk may include, for instance, may be a subject in a geographic location known to put subjects at risk of a disease or condition, for example, risk of infection by a microbial agent, virus, bacteria, or parasite etc.; a subject having a family and/or personal medical history of the disease or condition; a subject exposed to agents that are expected or known to increase risk of the disease or condition; and/or a subject who has previously been treated for the disease or condition and who may be considered by a medical professional to be at risk for recurrence or a chronic disease state, or infection.

In some embodiments of the invention, a treatment of a subject is a prophylactic treatment and in certain embodiments, a subject is selected for treatment with a nanoparticle vaccine of the invention at least in part on the basis that the subject has been exposed to an agent such as an infective agent. In some embodiments of the invention, the subject who is treated with administration of a nanoparticle vaccine of the invention has been diagnosed with a bacterial, viral, fungal, or other microbial infection. In certain embodiments of the invention, the subject who is treated with administration of a nanoparticle vaccine of the invention has been diagnosed with cancer, an autoimmune disease, or other disease or condition that may be treated by stimulating an immune response in the subject.

Treatment

The invention in some aspects relates to methods for stimulating an immune response and reducing a disease or condition in a subject. As used herein the term "reducing" means lowering one or more of the likelihood and severity of the disease or condition in a subject. A nanoparticle composition of the invention is also referred herein as a "nanoparticle vaccine", and when administered to a subject it acts in the subject to stimulate the subject's immune system to produce antibodies and to provide immunity against one or more diseases or conditions, without inducing the disease or condition. In some embodiments of the invention, a nanoparticle vaccine may comprise a plurality of one or more nanoparticles of the invention. In certain embodiments of the invention a nanoparticle vaccine may include a plurality of one type of nanoparticle of the invention. In other embodiments of the invention, a nanoparticle vaccine may include a plurality of each of two of more different nanoparticles of the invention, for example, two or more nanoparticles that differ from each other in their antigen and/or adjuvant combinations.

A presence or level of a disease or condition, such as an infection, cancer, auto-immune condition, etc., in a subject can be determined and compared to control values to assess the need for stimulation of an immune response in a subject or to ascertain the efficacy of a nanoparticle treatment of the invention. For example, likelihood of a disease or condition in a subject(s) not treated with a nanoparticle vaccine of the invention can be compared to the likelihood of the disease or condition in a treated subject to determine efficacy of a nanoparticle vaccine of the invention. Similarly, control values such presence, contagiousness, severity, etc. of a disease or condition can be compared with presence, contagiousness, severity, etc. following treatment with a nanoparticle vaccine of the invention as a measure of the effectiveness of the nanoparticle and/or treatment.

A control may be a predetermined value, which can take a variety of forms. It can be a single cut-off value, such as a median or mean. It can be established based upon comparative groups, such as in groups not having the disease or condition, groups not being exposed agents that result in the disease or condition and groups having the disease or condition, groups known to have been exposed to an agent that may result in the disease or condition. Another example of comparative groups may be groups having one or more symptoms or a diagnosis of the disease or condition, for example a disease such as a microbial infection, and groups without having one or more symptoms of or a diagnosis of the discase or condition, (e.g., the microbial infection). Another comparative group may be a group with a personal medical history of a disease or condition (e.g., a microbial infection, cancer, auto immune disease, etc.) and a group without such a personal medical history. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk and the lowest level of actual infection and the highest quadrant or quintile being individuals with the highest risk and highest levels of actual infection.

The predetermined value, of course, will depend upon the particular population selected. For example, an apparently healthy population will have a different "normal" range than will a population that is known to have been exposed to a microbial infection, or known to have cancer, etc. Accordingly, the predetermined value selected may take into account the category in which an individual subject falls. Appropriate ranges and categories can be selected with no more than routine experimentation by those of ordinary skill in the art. As used herein, "abnormal" means significantly different as compared to a normal control. By abnormally low likelihood of developing a disease or condition, e.g., a microbial infection it is meant low relative to a selected control, and may include an decrease in likelihood of having the disease or condition (for example after nanoparticle vaccine administration) at least 0.1%, 0.5%, 1%, 5%, 10%, 20%, 30%, 40%, 50%, 60%, 70%, 80%, 90%, or 100%, in a subject as compared to the level of infection in a non-vaccinated normal control.

Treatment of a subject with a nanoparticle vaccine of the invention may reduce severity or eliminate a disease or condition in the treated subject compared to the severity or presence of the disease or condition in an untreated control subject. Such a reduction may include a decrease of at least 0.5%, 1%, 5%, 10%, 20%, 30%, 40%, 50%, 60%, 70%, 80%, 90%, 100% of the severity/symptoms or presence of the disease or condition in the treated subject compared to an untreated control subject.

Treatment of a subject with a nanoparticle vaccine of the invention may reduce the likelihood of a disease or condition in the treated subject compared to the likelihood of the disease or condition in an untreated control subject. Such a reduction may include a decrease of at least 0.5%, 1%, 5%, 10%, 20%, 30%, 40%, 50%, 60%, 70%, 80%, 90%, 100% of the likelihood of the disease or condition in the treated subject compared to an untreated control subject.

As used herein, the terms "treat", "treated", or "treating" when used with respect to a disease or condition of a subject may refer to a prophylactic treatment that decreases the likelihood of a subject developing the disease or condition, and also may refer to a treatment after the subject has developed the disease or condition in order to eliminate or reduce the level, severity, length, infectivity, of the disease or condition, prevent the disease or condition from becoming more advanced (e.g., more severe), and/or to slow the progression of the disease or condition compared to in the absence of the nanoparticle vaccine therapy of the invention.

A nanoparticle vaccine of the invention may be administered to a subject singly or in combination with one or more additional compounds. In some embodiments, a nanoparticle vaccine of the invention may act in a synergistic manner with one or more other vaccines, therapeutic agents, actions, activities, or treatments and increase the effectiveness in the subject of the one or more therapeutic agents, actions, activities, or treatments. Thus, for example, a nanoparticle vaccine of the invention to treat a microbial infection may be administered with anther compound that also treats the microbial infection. A nanoparticle vaccine of the invention may act synergistically to increase the effectiveness of one or more agents or treatments that can be administered to treat a disease or condition for which the vaccine is administered. A nanoparticle vaccine of the invention may also act synergistically to increase the effectiveness of one or more other vaccines that can be administered to prevent development of a disease or condition for which the other vaccine is administered.

Nanoparticle vaccines of the invention described herein can be used alone or in conjugates or compositions with other molecules such as targeting agents and/or labeling agents in treatment methods of the invention. A non-limiting example of a targeting agent that may be included in a nanoparticle vaccine of the invention is a B-cell population-targeting antigen. In certain embodiments of the invention, a B-cell population-targeting antigen may be included in a nanoparticle that includes one or more adjuvants, but does not include any additional antigens. In certain embodiments of the invention, a B-cell population-targeting antigen may be included in a nanoparticle that includes one or more additional antigens, but does not include any adjuvants. In certain embodiments of the invention, a B-cell population-targeting antigen may be included in a nanoparticle that includes one or more adjuvants and one or more antigens.

Labeling agents may be used in methods and nanoparticles of the invention to determine the location of nanoparticles after administration and may be used to assess the delivery and location of treatment compounds such as nanoparticles of the invention that have been administered to a subject. Procedures for attaching and utilizing labeling agents such as enzymatic labels, dyes, radiolabels, etc. are well known in the art. [See for example, Dobrovolskaia et. al., 2008 *Mol Pharm* 5(4): 487-95].

Treatment methods of the invention that include administration of a nanoparticle vaccine of the invention to a subject can be used at any stages of a disease or condition in a subject including, early-stage, mid-stage, and late-stage of the disease or condition including all times before and after any of these stages. For example, a nanoparticle vaccine of the invention may be administered to a subject in advance of potential contact with an infective agent, or before the onset of a disease or condition such as a cancer, or autoimmune disorder as a preventive treatment. Similarly, a nanoparticle vaccine of the invention may be administered to a subject after the subject has been exposed to a microbial infective agent, or after the subject has a cancer or autoimmune disease or condition. Methods of the invention may also be used for subjects who have previously been treated with one or more other medicaments that were not successful, were minimally successful, and/or are no longer successful at slowing or stopping progression of the disease or condition in the subject.

Some aspects of the invention may include administration of a nanoparticle vaccine that includes an effective amount of an adjuvant-free nanoparticle to treat a disease or condition. In certain embodiments of the invention, a plurality of one or more adjuvant-free nanoparticle may be administered in conjunction with a plurality of one or more adjuvant-containing nanoparticles of the invention and the administration may enhance the efficacy of the one or more adjuvant-containing nanoparticles. In some embodiments of the invention, an effective amount of an adjuvant-free nanoparticle vaccine of the invention may be administered to a subject in conjunction with one or more other vaccines that are not nanoparticle vaccines of the invention, and may enhance the efficacy of the one or more other vaccines, and the increase in efficacy may be additive, partially additive, or synergistic. As used herein, administration in conjunction with another vaccine may include co-administration of two or more vaccines at the same time, or administration of one vaccine prior to or after another vaccine.

Some aspects of the invention may include administration of a nanoparticle vaccine that includes an effective amount of an adjuvant-only nanoparticle to treat a disease or condition. In certain embodiments of the invention, a plurality of one or more adjuvant-only nanoparticle may be administered in conjunction with a plurality of one or more antigen-containing nanoparticles of the invention and the administration may enhance the efficacy of the one or more antigen-containing nanoparticles. In some embodiments of the invention, an effective amount of an adjuvant-only nanoparticle vaccine of the invention may be administered to a subject in conjunction with one or more other vaccines that are not nanoparticle vaccines of the invention, and may enhance the efficacy of the one or more other vaccines, and the increase in efficacy may be additive, partially additive, or synergistic. As used herein, administration in conjunction with another vaccine may include co-administration of two or more vaccines at the same time, or administration of one vaccine prior to or after another vaccine.

Effective Amounts for Treatments

The invention, in part, also includes methods of administering to a subject in need of immune stimulation to treat a disease or condition, an effective amount of nanoparticles of the invention to treat the disease or condition. An "effective amount for treating a disease or condition" is an amount necessary or sufficient to realize a desired biologic effect. For example, an effective amount of a nanoparticle vaccine of the invention could be that amount necessary to (i) slow or halt progression of the disease or condition; or (ii) reverse one or more symptoms of the disease or condition. For example, a reduction in symptoms of an infection such as a mycobacterial infection may include a reduction in the level of fever, chills, vomiting, diarrhea, etc. According to some aspects of the invention, an effective amount is that amount of a nanoparticle vaccine (e.g., amount of nanoparticles) of the invention alone or in combination with another medicament or treatment, which when combined or co-administered or administered alone, results in a therapeutic response in the disease or condition, either in the prevention or the treatment of the disease or condition. The biological effect may be the amelioration and or absolute elimination of symptoms resulting from the disease or condition. In another embodiment, the biological effect is the complete abrogation of the disease or condition, as evidenced for example, by a diagnostic test that indicates the subject is free of the disease or condition.

Typically an effective amount of a nanoparticle of the invention to treat a disease or condition such as a cancer, microbial infection, auto immune disease or other disease or condition will be determined in clinical trials (for treating subjects), establishing an effective dose for a test population versus a control population in a blind study, etc. It will be understood that an effective amount of a nanoparticle can be also described in terms of an effective amount of one or more antigens and/or one or more adjuvants that make up the nanoparticle. Thus, in some embodiments an effective amount of a nanoparticle can be determined based, at least in part, on the amount of antigen and/or adjuvant in the particular type of nanoparticle. In some embodiments of the invention, an effective amount will be that amount that results in a desired response, e.g., an amount that diminishes the presence or likelihood of the disease or condition in a subject. Thus, an effective amount of a nanoparticle vaccine of the invention to treat a disease or condition in a subject may be the amount that when administered to the subject decreases the presence or likelihood of the presence of the disease or condition in the subject to a level that that is below the level that would occur in a subject without the administration of the nanoparticle vaccine of the invention. In the case of treating a disease or condition the desired response may be reducing or eliminating one or more symptoms of the disease or condition in a subject. The reduction or elimination may be temporary or may be permanent. The status of the disease or condition can be monitored using methods of determining the diagnosis, disease status, severity of the disease or condition in a subject. In some aspects of the invention, a desired response to treatment of the disease or condition can be delaying the onset or even preventing the onset of the disease or condition.

An effective amount of a nanoparticle vaccine of the invention to treat an infection, cancer, auto-immune disease, or other disease or condition may also be determined by assessing physiological effects of administration on a subject, such as a decrease of the infection, cancer, etc. in the subject following administration. Assays suitable to determine efficacy of a nanoparticle vaccine of the invention will be known to those skilled in the art and can be employed for measuring the level of the response to a treatment and an effective amount of a nanoparticle to administer to a subject, can be modified based, at least in part, on such measurements.

For example, in a subject having a microbial infection an effective amount of a nanoparticle or nanoparticle vaccine of the invention may be the amount that avoids the onset of, or reduces severity of fever, vomiting, chills, etc. It will be understood that in some instances the invention contemplates single administration of a nanoparticle vaccine of the invention and in some instances the invention contemplates multiple administrations of a nanoparticle vaccine. In a non-limiting example, a nanoparticle of the invention may be administered in a prime dose and a boost dose, although in some instances a single administration of a nanoparticle of the invention provides sufficient delivery of the antigen and adjuvant, that no boost dose is required. Numerous examples of suitable dose administration schedules for vaccines are known in the art and can be used in conjunction with nanoparticle vaccines of the invention.

The amount of a treatment may be varied for example in a treatment of a subject, by increasing or decreasing the amount of administered nanoparticles, by changing the therapeutic nanoparticle vaccine composition administered, by changing the route of administration, by changing the dosage timing, and so on. The effective amount will vary with the particular disease or condition being treated, the age and physical condition of the subject being treated; the severity of the disease or condition, the duration of the treatment, the nature of the concurrent therapy (if any), the specific route of administration, and additional factors within the knowledge and expertise of the health care professional and/or practitioner.

An effective amount of a nanoparticle vaccine of the invention in the treatment of a disease or condition or in the reduction of the risk of developing a disease or condition may vary depending upon the specific nanoparticles used, the mode of delivery of the nanoparticles, the combination of antigens and adjuvants in the nanoparticle, the amount or dose of each antigen and adjuvant that is delivered in the nanoparticle, and whether the nanoparticle vaccine is used alone or in combination with another treatment or therapy. A skilled artisan can empirically determine the effective amount of a particular nanoparticle vaccine of the invention without necessitating undue experimentation. Combined with the teachings provided herein, by choosing among the various active nanoparticles of the invention and weighing factors such as potency, relative bioavailability, subject body weight, severity of adverse side-effects and preferred mode of administration, an effective prophylactic or treatment regimen can be planned that does not cause substantial toxicity and yet is effective to treat the particular subject.

Nanoparticles of the invention may be administered in formulations or compositions, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the nanoparticles and nanoparticle vaccines of the invention may be administered in a pharmaceutical composition and the invention, in part, provides pharmaceutical compositions. Pharmaceutical compositions are sterile compositions that comprise the nanoparticles of the invention, optionally in a pharmaceutically acceptable carrier. Pharmaceutically acceptable carriers are well known to those of ordinary skill in the art. As used herein, a pharmaceutically acceptable carrier means a non-toxic material that does not interfere with the effectiveness of the biological activity of the active ingredients, e.g., the ability of the nanoparticles of the invention to treat disease or condition. The term "pharmaceutically acceptable carrier" means one or more compatible solid or liquid filler, diluents or encapsulating substances that are suitable for administration to a human or other subject contemplated by the invention. The term "carrier" as used herein, means an organic or inorganic ingredient, natural or synthetic, with which nanoparticles are combined to facilitate administration.

Non-limiting examples of pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

Modes of Nanoparticle Administration

A nanoparticle pharmaceutical composition of the invention, (which may also be referred to herein as a nanoparticle vaccine of the invention), may include a buffering agent, examples of which, though not intended to be limiting, may include acetic acid and a salt (1-2% w/v); citric acid and a salt (1-3% w/v); boric acid and a salt (0.5-2.5% w/v); and phosphoric acid and a salt (0.8-2% w/v). A pharmaceutical composition may also include a preservative, non-limiting examples of which may include benzalkonium chloride (0.003-0.03% w/v); chlorobutanol (0.3-0.9% w/v); and parabens (0.01-0.25% w/v). Additional suitable buffering agents and preservatives are known in the art and may be used in pharmaceutical compositions and methods of the invention.

A variety of administration routes are available with which to administer a nanoparticle vaccine to a subject. The particular mode selected will depend, at least in part, on the particular nanoparticle selected, the particular condition being treated and the dosage required for therapeutic efficacy. The methods of administering a nanoparticle vaccine of the invention may include any mode of administration that is medically acceptable, meaning any mode that produces effective levels of a desired response without causing clinically unacceptable adverse effects. Modes of administration that may be used with nanoparticles and methods of the invention include, but are not limited to parenteral administration, such as, subcutaneous injections, intravenous, intramuscular, intraperitoneal, intraventricular, intracranial, intrathecal, intrasternal injection or infusion techniques. Other modes of administration of nanoparticles of the invention include, but are not limited to, oral, mucosal, rectal, vaginal, sublingual, intranasal, intratracheal, inhalation, ocular, transdermal, etc.

For oral administration, the nanoparticle vaccines of the invention can be formulated readily by combining the particles with pharmaceutically acceptable carriers well known in the art. Such carriers allow formulation as tablets, pills, dragees, capsules, liquids, gels, syrups, slurries, films, suspensions and the like, for oral ingestion by a subject to be treated. Suitable excipients that may also be included in formulations for administration of nanoparticles of the invention may include, but are not limited to fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). An oral formulation for administration of a nanoparticle of the invention to a subject may also be formulated in saline or buffers for neutralizing internal acid conditions or may be administered without any carriers.

For buccal administration, the compositions of nanoparticle vaccines of the invention may take the form of tablets or lozenges formulated in a conventional manner.

Nanoparticle vaccines of the invention may also be administered by inhalation. Pharmaceutical compositions for inhalation may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Pharmaceutical composition for inhalation may also be delivered in the form of a dry powder, as described (Labiris et al. 2003. *Br. J. Clin. Pharmacol.* 56(6):600-612.). In the case of the dry powdered inhaler (DPI) the dosage unit may be determined by providing a valve to deliver a metered amount.

For delivery of a nanoparticle pharmaceutical composition of the invention systemically, the composition may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances that increase the viscosity of the suspension, such as sodium carboxymethyl cellulose, sorbitol, or dextran. Alternatively, suspensions of nanoparticles of the invention may be prepared as oil-based suspensions. Suitable solvents or vehicles may include fatty oils such as sesame oil, or synthetic fatty acid esters, such as ethyl oleate or triglycerides.

Nanoparticle and nanoparticle vaccines of the invention may be prepared in powder form or lyophilized form that can be diluted (e.g., reconstituted) with a suitable vehicle, e.g., sterile pyrogen-free water, before use. The nanoparticle pharmaceutical compositions of the invention may also be formulated in rectal or vaginal compositions such as suppositories or retention enemas, e.g., containing conventional suppository bases such as cocoa butter or other glycerides.

Nanoparticle Administration/Dosing

As described herein, single doses of nanoparticle pharmaceutical compositions of the invention are contemplated as are instances in which a subject is administered a single dose plus a booster dose, and instances in which a subject is administered multiple doses. In addition, multiple doses of compounds of the invention are also contemplated. In some instances, a compound of the invention can be administered at least daily, every other day, weekly, every other week, monthly, yearly, every at least 2, 3, 4, 5, 10, 15, 20, 30, 40 years, etc. to a subject. Doses may be administered once per day or more than once per day, for example, 2, 3, or more times in one 24 hour period.

Nanoparticle pharmaceutical compositions of the invention to treat subjects may be administered alone, in combination with other nanoparticles of the invention, and/or in combination with other vaccines, drug therapies, or other treatment regimens that are administered to subjects. Pharmaceutical compositions for use in subjects in the foregoing methods may be sterile and contain an effective amount of a compound of the invention to produce the desired response in a unit of weight or volume suitable for administration to a subject.

The doses of a nanoparticle pharmaceutical composition of the invention (e.g., a nanoparticle vaccine) to treat a disease or condition, (for example, a mycobacterial infection, cancer, an auto immune condition) can be chosen in accordance with different parameters, in particular in accordance with the mode of administration used and the state of the subject. Other factors may include the desired period of treatment. In the event that a response in a subject is insufficient at the initial doses applied, higher doses (or effectively higher doses by a different, more localized delivery method or route) may be employed to the extent that subject tolerance permits.

Antigen and Adjuvant Dose

Nanoparticles of the invention allow reduced amounts of adjuvants to be administered to subjects in need of immune stimulation while retaining or improving efficacy. It is advantageous to treat a disease or condition using a lower amount of adjuvant in that administration of less adjuvant results in fewer side effects in a subject than arise when administering higher amounts of adjuvant using an administration means other than nanoparticles of the invention. Features and design of nanoparticles of the invention can make their included antigens and adjuvants up to 1000 times more potent when administered to a subject, than delivery of the antigens and adjuvants using a delivery means that does not utilize nanoparticles of the invention, see for example, results shown in FIG. 2B. Thus, the effective dose of one or more antigens and the effective dose of one or more adjuvants in a nanoparticle vaccine of the invention may be lower than would be expected when administering the one or more antigens and the one or more adjuvants not as part of a nanoparticle of the invention.

An antigen dose effective to stimulate the immune system and elicit an antibody response in a subject may range from one femtogram to milligrams. (See Schnare et al, *Nature Immunol.* 2, 947-950 (2001); Matriano et al, *J. Pharm. Res,*

19(1), 63-70 (2002); Fifis et al. *J Immunol* 173(5): 3148-3154 (2004); Klinman et al, *Vaccine* 17(1) 19-25 (1999); Poolman et al. *Expert Reviews Vaccines* 12(12): 1379-1394 (2013).) Thus doses of antigen useful in treatment methods of the invention may be in a range of 1 microgram 15 to 1 milligram, 1 microgram to 5 milligrams, 50 micrograms to 1 milligram, 50 micrograms to 5 milligrams, 500 micrograms to 5 milligrams, 1 femtogram to 5 nanograms, 1 femtogram to 500 nanograms, 1 femtogram to 100 nanograms, 1 femtogram to 10 nanograms, 1 femtogram to 1 nanograms, 50 femtograms to 100 nanograms, 50 femtograms to 50 nanograms, 50 femtograms to 5 nanograms, 50 femtograms to 1 nanogram, 500 femtograms to 500 nanograms, 500 femtograms to 100 nanograms, 500 femtograms to 50 nanograms, 5000 femtograms to 500 nanograms, 5000 femtograms to 100 nanograms, 5000 femtograms to 50 nanograms, 5000 femtograms to 5 nanograms, 5000 femtograms to 1 nanogram, 1 femtogram to 1 milligram, 1 femtogram to 5 milligrams, 1 femtogram to 500 micrograms, 1 femtogram to 100 micrograms, 1 femtogram to 10 micrograms, 1 femtogram to 1 microgram, 50 femtograms to 100 micrograms, 50 femtograms to 50 micrograms, 50 femtograms to 5 micrograms, 50 femtograms to 1 microgram, 500 femtograms to 500 micrograms, 500 femtograms to 100 micrograms, 500 femtograms to 50 micrograms, 5000 femtograms to 500 micrograms, 5000 femtograms to 100 micrograms, 5000 femtograms to 50 micrograms, 5000 femtograms to 5 micrograms, or 5000 femtograms to 1 microgram.

Adjuvant doses in a nanoparticle treatment method of the invention may be lower than those generally administered in conjunction with antigens to treat a disease or condition. In some instances, the dose of adjuvant may be about 75% or about 50% or as low as 10% of the amounts that are necessary when not administered in a nanoparticle of the invention. In some embodiments of the invention, the dose of adjuvant may be 10-fold, 20-fold, 30-fold, 40-fold, 50-fold, 60-fold, 70-fold, 80-fold, 90-fold, 100-fold, 250-fold, 500-fold, 750-fold, 1000-fold or more less than is necessary than when the adjuvant is administered using a means other than as part of a nanoparticle of the invention.

When treating a subject, a pharmaceutical nanoparticle vaccine dosage may be adjusted by an individual health care provider or veterinarian, particularly in the event of any complication. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

An amount/dose of antigen and/or adjuvant that are effective to treat a disease or condition can be determined using routine methods. In certain embodiments of the invention, an amount of adjuvant administered to a subject is in a range from 1 femtogram to 5 milligrams. In certain embodiments of the invention, an amount of antigen administered to a subject is in a range between 1 femtogram to 5 milligrams to treat a disease or condition.

Methods of Preparing Nanoparticles

Methods of producing a nanoparticle of the invention are also contemplated. Generally, the production methods include preparing a polymer substrate that may, in some embodiments of the invention, include a biodegradable polymer and at least 1, 2, 3, 4, 5, 6, 7, 8, 9, 10, 50, 90, 150, or more antigens. An antigen may be an antigen of interest to treat a specific disease or condition. One or more adjuvants may be selected based at least in part, on the adjuvant's ability to enhance an immune response that is elicited by the antigen when both the adjuvant and antigen are administered to a subject. Thus, an adjuvant may be selected that works in cooperation with one or more antigens (either an antigen that is included in a nanoparticle of the invention, or an antigen that is administered to a subject using a different vehicle or vaccine) to elicit an immune response in a subject to which it is administered. In certain embodiments of nanoparticle production, the selected adjuvant may be encapsulated with the polymer substrate that includes the biodegradable polymer and the 1 or more antigens. In certain embodiments of the invention, nanoparticle production includes preparing the polymer substrate such that at least one antigen is positioned in part, external to the outer surface of the produced nanoparticle. As used herein, the phrase "at least a portion" means at least 5%, 10%, 15%, 20%, 25%, 30%, 35%, 40%, 45%, 50%, 55%, 60%, 65%, 70%, 75%, 80%, 90%, but less than 100%.

In producing an embodiment of a nanoparticle of the invention, a least a portion of the at least one antigen in the polymer substrate is positioned internal to the outer surface of the produced nanoparticle. Non-limiting examples of biodegradable polymer that may be included when producing nanoparticles of the invention are poly(lactic-co-glycolic acid) (PLGA), poly L-lactic acid (PLLA), poly(lactic acid) (PLA), poly(glycolytic acid) (PGA), polycaprolactone, polyglycolide, polylactic acid, poly-3-hydroxybutyrate, polyanhydrides, and hyaluronans. Non-limiting examples of antigens and adjuvants that may be included when producing nanoparticle using methods of the invention are described elsewhere herein. In certain embodiments of the invention a nanoparticle may be prepared that includes at least 1, 2, 3, 4, 5, 6, 7, 8, 9, 10, 20, 30, 40, 50, 60, 70, 80, 90, 100, 150, 200, or more antigens and does not include any adjuvants. In certain embodiments of the invention a nanoparticle may be prepared that includes at least 1, 2, 3, 4, 5, 6, 7, 8, 9, 10, 20 or more adjuvants and does not include any antigens.

Nanoparticles of the invention can be prepared with a predetermined amount of one or more antigens, and a predetermined amount of one or more adjuvants. Examples of preparation methods, although not intended to be limiting, are set forth herein in the Examples section. Alternative methods of nanoparticle production are known in the art, which may, in combination with the disclosure provided herein, be suitable for preparing nanoparticles of the invention.

Kits

Also within the scope of the invention are kits that comprise one or more nanoparticle compositions of the invention and instructions for use. Kits of the invention may include one or more of a nanoparticle compound of the invention that may be used to treat a disease or condition. Kits containing nanoparticle compounds of the invention can be prepared for use in treatment methods for subjects. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more nanoparticles of the invention. A second container means or series of container means may contain a solvent, medium, solvate, etc., that may be added to the nanoparticle composition for use and administration. A second container means may in some embodiments include an additional therapeutic agent for administration in conjunction (simultaneous, prior, or successive) with a nanoparticle composition of the invention.

A kit of the invention may also include instructions. Instructions typically will be in written form and will provide guidance for carrying out a treatment embodied by the kit and for making a determination based upon that treatment.

EXAMPLES

Example 1

Nanoparticle Preparation

Nanoparticles were prepared using 250 µl of 0.8 mg/ml polysaccharide (S. pneumoniae polysaccharide serotype 3 from ATCC, SpPS) and 0.5 mg/ml BSA solution in 8 mM citrate buffer (pH=8.0). Glycolipids included in the nanoparticles included either αGalactosylceramide (CAS #158021-47-7) or βGlucosylceramide (CAS #887907-50-8). The polysaccharide and BSA solution was added into 1 mL of PLGA (with/without lipid 25 µL/125 µg) solution in dichloromethane (50 mg/ml) and then sonicated once on ice by a microtip sonicator (85% amplitude ~100 w) for 20 seconds (5 seconds on 3 seconds off). The first emulsion was quickly dropped into 4 ml of 10% sucrose solution and sonicated on ice for 20 seconds (5 seconds on, 3 seconds off) for 3 times (total 60 seconds) to form the second emulsion. The organic solvent within the emulsion was removed by a rotary evaporator using water pump over one hour. The obtained particle solution was then centrifuged for 3 times at 3000 ref in 50 mL Eppendorf tube for 4 minutes each to remove unbound lipid and/or polysaccharide. Between each centrifugation, the suspension was sonicated using sonication bath for 3-5 minutes to break down the pellets that formed after centrifugation. The final suspension contained 25 mL for each sample in double-distilled water. The suspension was further diluted to 75 mL, and 25 mL was decanted for characterization. Nanoparticle size and glycolipid content were characterized by transmission electron microscopy (FIGS. 1A and B), scanning electron microscopy (SEM) (FIG. 1C) and mass-spectrometry (MS) (not shown).

Nanoparticle Assessment

Figure 1C:
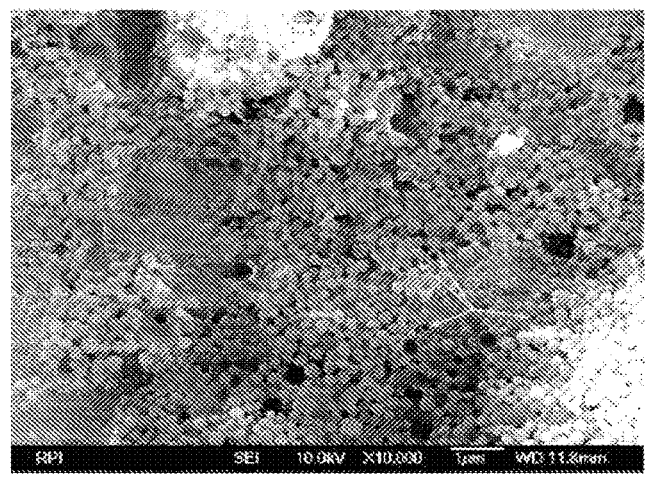

SEM samples were prepared by adding one drop of nanoparticle solution onto a silicon wafer and dried under vacuum overnight. The dried samples were imaged using a field emission scanning electron microscope (FE-SEM) JSM-6335 (Tachikawa, Tokyo, Japan) (FIG. 1C). All samples were sputter-coated with 10 Å of palladium (Denton Desk II, Moorestown, N.J.) prior to imaging. Images were obtained at a working distance of 15 cm using an acceleration voltage of 10 kV.

AlphaGalCer and βGlcCer were quantified by a LC-MS/MS method running in multiple reaction monitoring (MRM) mode. Chromatographic separation was achieved using Waters HPLC column (BEH C8, 3 mm×50 mm) (Waters Corporation, Milford, Mass.). The mobile phase was A: 5 mM ammonium formate in water with 0.2% formic acid; B: 5 mM ammonium formate in methanol with 0.2% formic acid. The gradient started from 85% B to 100% B in 5 min, then kept at 100% B for 3 min, then reset to 85% B. The LC flow rate was 250 uL/min and 5 ul sample was injected for the LC-MS/MS analysis. Standards of αGalCer and βGluCer at various concentrations were used to make the external calibration curve used for quantification.

The immunogenicity of the various nanoparticle preparations was assessed as described in later examples.

Example 2

In Vitro Immunogenicity Study of Glycolipid Containing Nanoparticles.

Control nanoparticles contained αGalCer and βGlcCer inside the center of a PLGA nanoparticle. These particles were assembled as described in Example 1 with the omission of polysaccharides from the BSA solution in step 1. These control nanoparticles were tested in preliminary in vitro studies to determine effective dose ranges for activation of both iNKT and B cells.

In Vitro Assay.

Figure 2A:
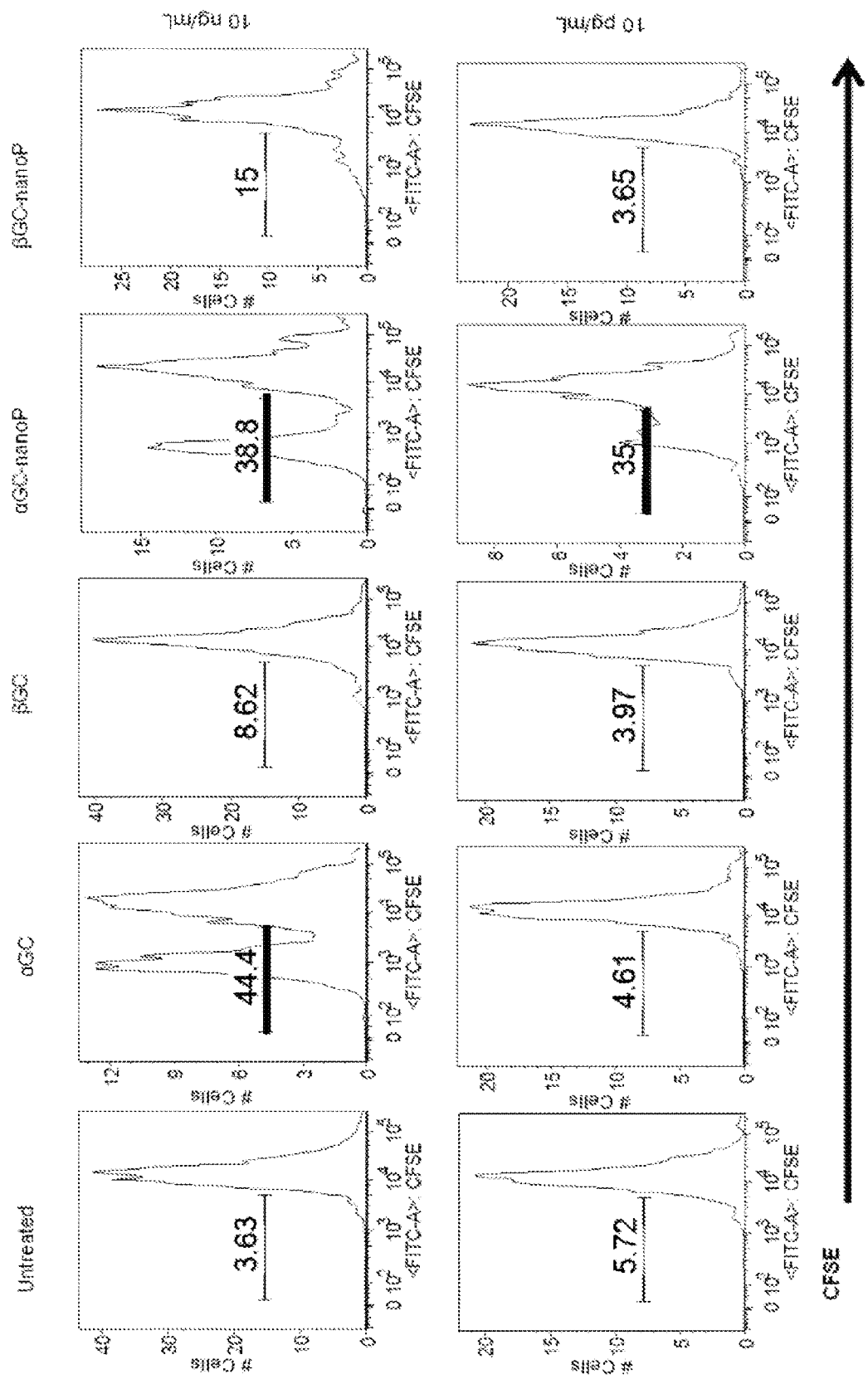
FIG. 2A shows results of fluorescence-activated cell sorting (FACS) to determine the percentage of CD1dtet+TCRβ+iNKT cells that dilute CFSE as a measure of proliferation.
Figure 2B:
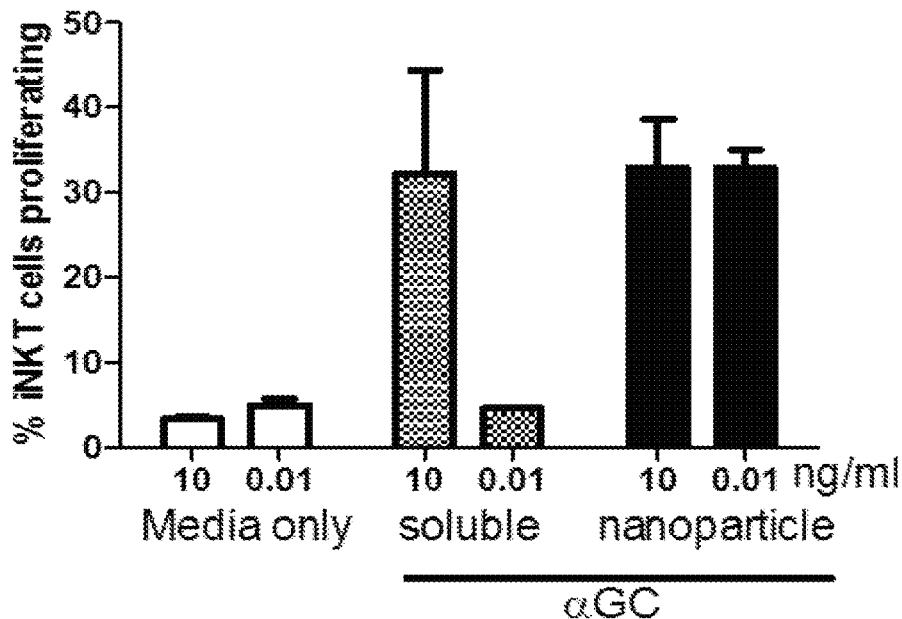
FIG. 2B is a graph showing a summary of the data in FIG. 2A.

Total spleen cells from WT C57BL/6 mice were removed, a single cell suspension was created, and red blood cells were lysed. Splenocytes were labeled with carboxyfluorescein succinimidyl ester (CFSE) using standard procedures and then cultured at $2\times10^6$ cells/well in a 96 well flat bottom tissue culture plate. At the initiation of this culture, cells were coincubated with 10 pg/ml or 10 ng/ml of αGalCer, βGlcCer, αGC-NanoP, βGC-NanoP, or left in media only. After three days of culture, cells were removed from the wells, labeled with fluorescently tagged lineage specific markers (anti-B220 for B cells and anti-TcRβ plus CD1d-tetramer for iNKT cells) and assessed for cell type specific CFSE dilution by FACS analysis. 44% of iNKT cells proliferated vigorously in response to soluble αGalCer at the 10 ng/ml dose, but were not responsive to the 10 pg/ml dose (FIG. 2A). In comparison, 39% of iNKT cells proliferated in response to αGC-NanoP at the 10 ng/ml dose and 35% responded vigorously to the 10 pg/ml dose. Results indicated that nanoparticle encapsulation of the αGC increased the sensitivity of the iNKT response 1000 fold (Summarized in FIG. 2B). In other wells of the same assay, it was clear that neither βGlcCer alone nor βGC-NanoP were stimulatory for iNKT cells at either dose tested (see FIG. 2A).

Figure 2C:
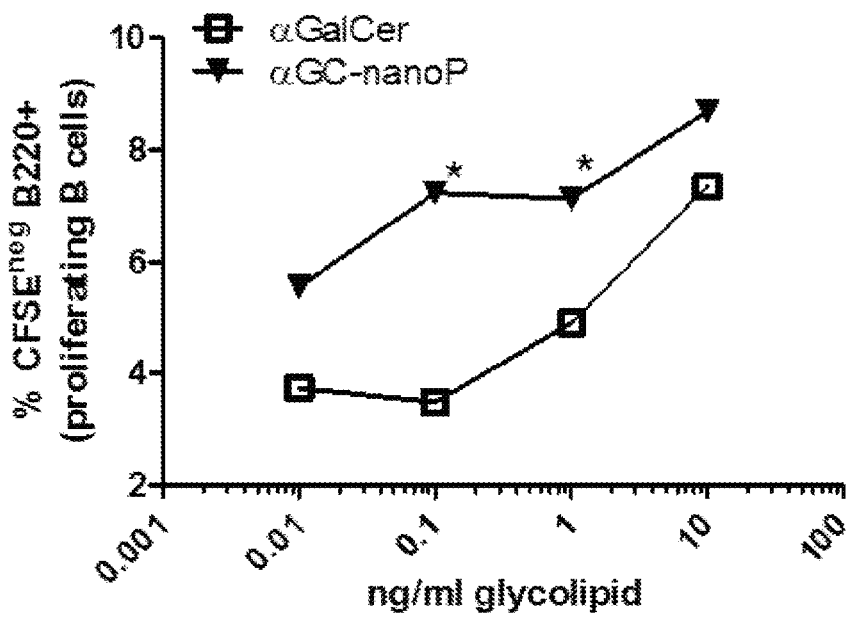
FIGS. 2C and 2D show the percentage of B220+ cells that dilute CFSE after 3 days of in vitro culture with soluble αGalCer and αGC-NanoP (FIG. 2C), or soluble βGlcCer and βGC-NanoP (FIG. 2D). Results shown are representative of 2 experiments, duplicate wells. *=p≤0.05 as compared to soluble glycolipid.
Figure 2D:
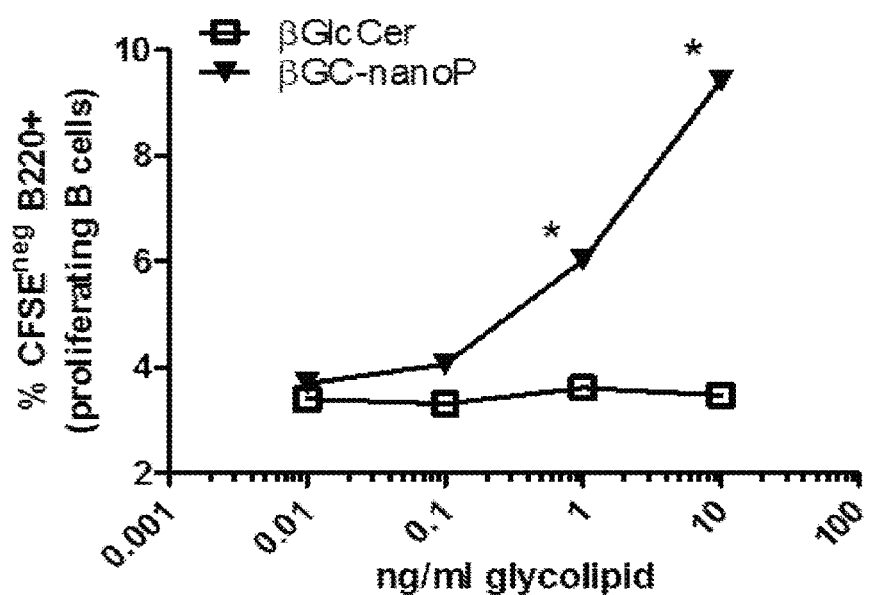

As further depicted in FIGS. 2C and D, αGalCer and βGlcCer also induced proliferation by splenic B cells. In vitro cultures set up as described above herein revealed that splenic B cells responded similarly as iNKT cells. B cells proliferated vigorously to both 10 ng/ml and 10 pg/ml of αGalCer when incorporated in the form of a nanoparticle, but only to the higher doses of soluble αGalCer. The response to βGlcCer was not as robust but B cells still proliferated strongly to 10 ng/ml βGlcCer in nanoparticles (βGC-NanoP) but not to the doses tested of soluble βGlcCer (see FIGS. 2C and 2D).

Example 3

In Vivo Immunogenicity Study of Nanoparticles Containing Both Glycolipid Adjuvant and Streptococcus pneumoniae Polysaccharide.

Figure 3A:
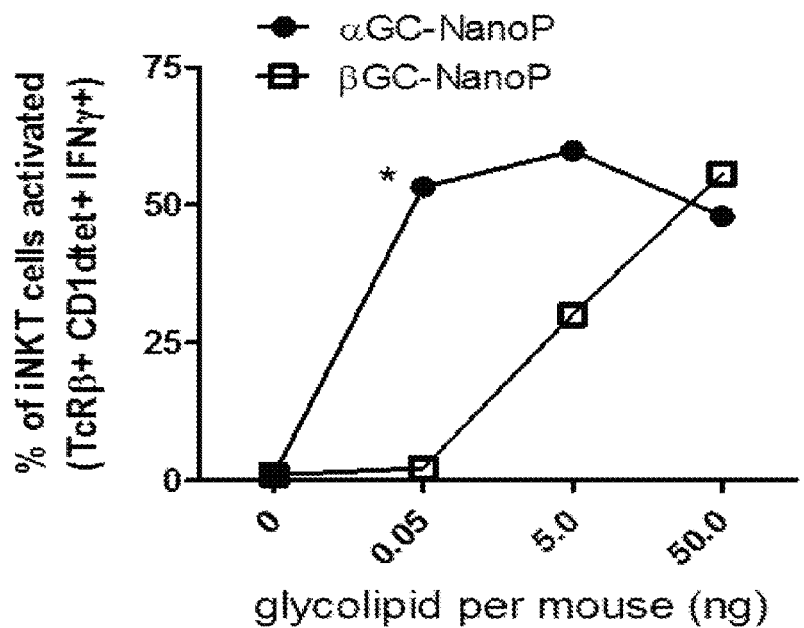
FIGS. 3A and 3B show percent of iNKT cells activated versus ng glycolipid per mouse. In results from the study, C57BL/6 WT mice vaccinated with either αGC-NanoPs or βGC-NanoPs showed splenic iNKT cells were activated in a dose-dependent manner after 4 hours. Surprisingly, the results showed that the usually very weak agonist βGlcCer stimulated robust levels of iNKT proliferation when encorporated into nanoparticles at the higher doses tested. In another experiment, nanoparticle preparations containing glycolipid plus polysaccharides from S. pneumoniae (αGC-SpPS-NanoP) also induced a robust IFNγ response by iNKT cells when administered i.v. WT C57BL/6 mice were immunized i.v. with NanoPs containing noted concentrations of glycolipid (FIG. 3B).

To assess the activation of iNKT cells in vivo by nanoparticles, groups of 5-10 C57BL/6 WT mice were immunized i.v. with nanoparticles containing 50 ng glycolipid. INKT cells from mice immunized with αGalCer-NanoP were robustly activated to produce IFNγ within four hours (FIG. 3A) at all doses tested. Nanoparticle preparations containing βGlcCer (βGC-NanoP) also induced robust iNKT cell activation. However, GlcCer is only a very modest agonist for iNKT cells, and thus the βGC-NanoP particles induced an in vivo response by iNKT cells which was 1000 fold lower than that induced by the αGC-NanoP particles. FIG. 3A shows the percent of CD1dtet+TCRβ+ iNKT cells that were determined by FACS to be IFNγ+ in spleen 4 hours after immunization with αGalCer or βGlcCer containing Nanoparticles (αGC-NanoP or fGC-NanoP, respectively). Results were also obtained showing the percent of CD1dtet+TcRβ+iNKT cells that were determined by FACS to be IFNγ+ in spleen 4 hours after immunization with αGalCer or βGalCer containing Nanoparticles that were also embedded with *S. pneumoniae* polysaccharides (αGC-SpPS-NanoP and βGC-SpPS-NanoP respectively).

Polysaccharides from the capsule of *Streptococcus pneumoniae* are long chains of sugars that are weakly immunogenic if administered alone, mostly because they are not recognized by peptide-specific helper T cells and must activate B cells in a T-independent manner [Weintraub, A. 2003 *Carbohydrate research* 338:2539-2547]. Large doses of polysaccharides, as in the Pneumovax vaccine, can induce moderate humoral immune responses, but their protective efficacy is modest at best [Jackson, L. A., et. al., 2003 *The New England journal of medicine* 348:1747-1755]. Alternatively, these polysaccharides are conjugated to antigenic peptides to recruit CD4 T cell help, and these formulations elicit increased humoral immune responses, which are more protective in humans [Whitney, C. G., et. al., 2003 *The New England journal of medicine* 348:1737-1746]. In embodiments tested, nanoparticles were designed to embed *S. pneumoniae* polysaccharides inside nanoparticles that contained glycolipid adjuvant (αGC-SpPS-NanoP and βGC-SpPS-NanoP) in order to recruit iNKT cells to provide help for polysaccharide-specific B cells and thus enhance the immunogenicity of these polysaccharides.

Figure 3B:
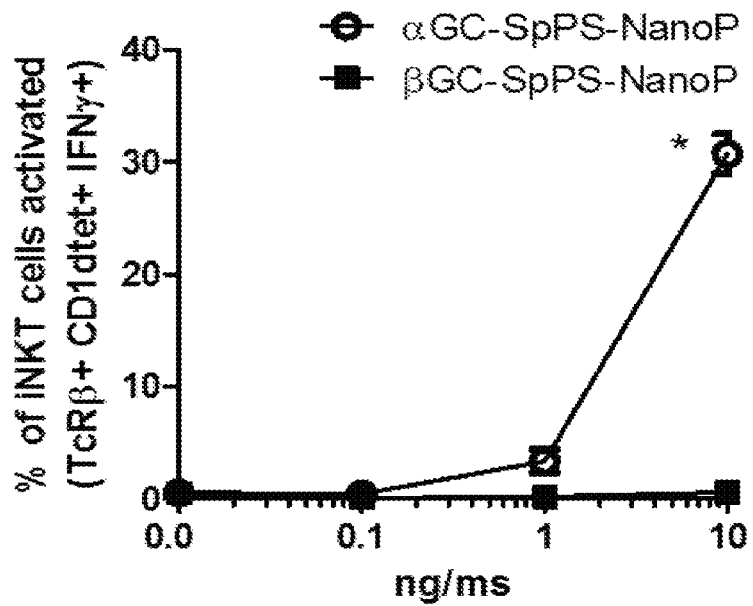

First, in vivo studies were performed to confirm that encapsulation of *S. pneumoniae* polysaccharides in nanoparticles containing glycolipid adjuvant (αGC-SpPS-NanoP and βGC-SpPS-NanoP) did not alter the adjuvanticity of the glycolipids. As shown in FIG. 3B, i.v. immunization of WT C57BL/6 mice with 10-1 ng/mouse of αGC-SpPS-NanoP induced dose-dependent IFNγ production by iNKT cells after 4 hours. Within this dose range, no IFNγ production by iNKT cells was elicited by βGC-SpPS-NanoP. Thus, nanoparticles that encapsulate the adjuvant αGalCer and were also embedded with *Streptococcus pneumoniae* polysaccharides robustly activated iNKT in vitro.

Example 4

Vaccination Study of Nanoparticles Containing Both Glycolipid Adjuvant and *Streptococcus pneumoniae* Polysaccharide.

A goal of this nanoparticle formulation was to direct iNKT cell activation towards a subset of antigen-specific B cells. In this example, *S. pneumoniae* polysaccharide was embedded in the glycolipid containing nanoparticles to serve as the B cell antigen. This approach was also a proof of principle for a myriad of other possible antigens.

To assess the ability of glycolipid containing, B cell antigen-embedded nanoparticles to activate the relevant B cell population, C57BL/6 WT mice were immunized with 50 ng glycolipid/mouse doses of nanoparticles. The mice were bled on days 10 and 17 after immunization and antibody titer determined by ELISA of serum samples.
Enzyme Linked Immunosorbent Assay (ELISA) Screening for Antigen-Specific Antibody Levels.

Microtiter wells were coated with saturating quantities of purified *S. pneumoniae* polysaccharide (serotype 3) from ATCC diluted in PBS. The plates were blocked with 5% BSA solution and then washed thoroughly with 0.1% tween/PBS wash buffer. Serum samples were diluted from 1:100-1:300,000 in 0.1% BSA/PBS and added to the microtiter wells overnight at 4° C. Plates were then washed and plate-bound antibody was detected with HRP labeled anti-IgG or anti-IgM. After 1 hour incubation, unbound detecting antibody was washed away and a horseradish peroxidase (HRP) substrate [2,2'-azino-bis(3-ethylbenzothiazoline-6-sulphonic acid) (ABTS) from Sigma (St. Louis, Mo.)] added per manufacturer's instructions. Absorbance was measured by Spectramax Microplate reader (Molecular Devices, Sunnyvale, Calif.) and titer was determined to be the lowest dilution which gave an O.D. higher than 2× background.

Vaccine formulations of nanoparticles which contain both αGalCer and SpPS were found to drive production of robust in vivo IgM anti-SpPS antibody responses detectable at day 10 (not shown) and day 17 after vaccination (FIG. 4A). C57BL/6 wild type (WT) mice were immunized as noted with nanoparticle preparations containing 50 ng glycolipid or equivalent volume for PLGA controls. In comparison, control mice receiving intramuscular (i.m.) vaccination with 0.5 μg Prevnar13 produced high titers of SpPS-specific IgG, very little IgM. (FIG. 4A,B). Control nanoparticles that contained only PLGA or PLGA plus SpPS induced no detectable increase in SpPS-specific IgG or IgM and αGC-PLGA nanoparticles only induced a modest increase in SpPS-specific IgM. Mice were subsequently boosted on day 47 with identical dose of NanoP or Prevnar13 and then systemically infected with a lethal dose of *S. pneumoniae* ($9.4 \times 10^4$ CFU per mouse) strain URF 918 i.v. on day 96 and followed to assess morbidity. Immunization with either Prevnar 13 or αGC-SpPS-NanoP enhanced survival of the mice in the vaccinated groups, while immunization with control NanoPs (PLGA, αGC-PLGA, or SpPS-NanoP) failed to provide significant protection (FIG. 4C). In short, vaccination with αGC-SpPS-PLGA NanoP induced a robust polysaccharide antigen-specific humoral immune response which protected the majority of mice against systemic infection with *S. pneumoniae*.

Importantly, these data demonstrated that encapsulation in nanoparticles increases the activity of the glycolipid adjuvants tested by 1000×, and greatly improved their ability to activate iNKT cells in vitro and in vivo. Furthermore, these data showed that a nanoparticle formulation containing glycolipid adjuvant and embedded with a B cell polysaccharide antigen activated iNKT cells and drove a concomitant antigen-specific B cell antibody response. Evidence also suggests these antibodies protect against infection with live bacteria.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A method of producing a nanoparticle capable of eliciting a greater immunoglobulin M response as compared to an immunoglobulin G response, the method comprising, (a) preparing a polymer substrate comprising a polysaccharide antigen derived from *Streptococcus pneumoniae* intercalated with a biodegradable polymer;

(b) selecting an adjuvant that in cooperation with the polysaccharide antigen is capable of eliciting an antibody response specific to the polysaccharide antigen in a subject, wherein the adjuvant is a natural or synthetic alpha-galactosylceramide compound; and (c) encapsulating the selected adjuvant with the polymer substrate to produce the nanoparticle capable of eliciting about 1000-fold greater immunoglobulin M response specific to the polysaccharide antigen as compared to an immunoglobulin G response specific to the polysaccharide antigen.

2. The method of claim 1, wherein at least a portion of the polysaccharide antigen in the prepared polymer substrate is positioned external to the outer surface of the produced nanoparticle.

3. The method of claim 1, wherein the biodegradable polymer is poly(lactic-co-glycolic acid) (PLGA), poly L-lactic acid (PLLA), poly(lactic acid) (PLA), poly(glycolytic acid) (PGA), polycaprolactone, polyglycolide, polylactic acid, poly-3-hydroxybutyrate, polyanhydrides, or hyaluronans.

* * * * *